(12) United States Patent
Gopferich et al.

(10) Patent No.: US 8,740,929 B2
(45) Date of Patent: *Jun. 3, 2014

(54) SPACING DEVICE FOR RELEASING ACTIVE SUBSTANCES IN THE PARANASAL SINUS

(75) Inventors: Achim Gopferich, Sinzing (DE); Werner Hosemann, Greifswald (DE)

(73) Assignee: Acclarent, Inc., Menlo Park, CA (US)

( * ) Notice: Subject to any disclaimer, the term of this patent is extended or adjusted under 35 U.S.C. 154(b) by 348 days.

This patent is subject to a terminal disclaimer.

(21) Appl. No.: 10/470,881

(22) PCT Filed: Feb. 6, 2002

(86) PCT No.: PCT/EP02/01228
§ 371 (c)(1),
(2), (4) Date: Feb. 4, 2004

(87) PCT Pub. No.: WO02/062269
PCT Pub. Date: Aug. 15, 2002

(65) Prior Publication Data
US 2004/0116958 A1 Jun. 17, 2004

(30) Foreign Application Priority Data
Feb. 6, 2001 (DE) .................... 101 05 592

(51) Int. Cl.
*A61L 31/16* (2006.01)
*A61L 31/10* (2006.01)

(52) U.S. Cl.
USPC ........................ 606/199; 424/425; 623/23.7

(58) Field of Classification Search
USPC ....................................................... 424/423
See application file for complete search history.

(56) References Cited

U.S. PATENT DOCUMENTS

| | | |
|---|---|---|
| 446,173 A | 2/1891 | Hancock |
| 504,424 A | 9/1893 | De Pezzer |
| 513,667 A | 1/1894 | Buckingham |
| 705,346 A | 7/1902 | Hamilton |
| 798,775 A | 9/1905 | Forsyth |
| 816,792 A | 4/1906 | Green et al. |
| 1,080,934 A | 12/1913 | Shackleford |
| 1,200,267 A | 10/1916 | Sunnergren |
| 1,650,959 A | 11/1927 | Pitman |
| 1,735,519 A | 11/1929 | Vance |
| 1,828,986 A | 10/1931 | Stevens |
| 1,878,671 A | 9/1932 | Cantor |
| 2,201,749 A | 5/1940 | Vandegrift |
| 2,525,183 A | 3/1947 | Robison |
| 2,493,326 A | 1/1950 | Trinder |
| 2,847,997 A | 8/1958 | Tibone |
| 2,899,227 A | 8/1959 | Gschwend |
| 2,906,179 A | 9/1959 | Bower |
| 2,995,832 A | 8/1961 | Alderson |
| 3,009,265 A | 11/1961 | Bezark |
| 3,037,286 A | 6/1962 | Bower |
| 3,173,418 A | 3/1965 | Baran |
| 3,347,061 A | 10/1967 | Stuemky |
| 3,376,659 A | 4/1968 | Asin et al. |
| 3,384,970 A | 5/1968 | Avalear |
| 3,393,073 A | 7/1968 | Reutenauer et al. |
| 3,435,826 A | 4/1969 | Fogarty |
| 3,469,578 A | 9/1969 | Bierman |
| 3,481,043 A | 12/1969 | Esch |
| 3,486,539 A | 12/1969 | Jacuzzi |
| 3,506,005 A | 4/1970 | Gilio et al. |
| 3,509,638 A | 5/1970 | Macleod |
| 3,515,888 A | 6/1970 | Lewis |
| 3,527,220 A | 9/1970 | Summers |
| 3,531,868 A | 10/1970 | Stevenson |
| 3,552,384 A | 1/1971 | Pierie et al. |
| 3,624,661 A | 11/1971 | Shebanow et al. |
| 3,731,963 A | 5/1973 | Pond |
| 3,792,391 A | 2/1974 | Ewing |
| 3,800,788 A | 4/1974 | White |
| 3,802,096 A | 4/1974 | Matern |
| 3,804,081 A | 4/1974 | Kinoshita |
| 3,834,394 A | 9/1974 | Hunter et al. |
| 3,850,176 A | 11/1974 | Gottschalk |
| 3,856,000 A | 12/1974 | Chikama |
| 3,859,993 A | 1/1975 | Bitner |
| 3,871,365 A | 3/1975 | Chikama |
| 3,894,538 A | 7/1975 | Richter |
| 3,903,893 A | 9/1975 | Scheer |

(Continued)

FOREIGN PATENT DOCUMENTS

| | | |
|---|---|---|
| CH | 668188 | 12/1988 |
| CN | 2151720 | 1/1994 |

(Continued)

OTHER PUBLICATIONS

Argon Medical. Maxxim Medical. Ad for Sniper EliteTM Hydrophilic Ni—Ti Alloy Guidewire (2001).

(Continued)

*Primary Examiner* — Michael G Hartley
*Assistant Examiner* — Nabila Ebrahim
(74) *Attorney, Agent, or Firm* — Frost Brown Todd LLC

(57) ABSTRACT

A spacing device for use in fenestrations of the paranasal sinus, the device including a sheath which forms a hollow body defining at least two apertures. The sheath includes at least one layer loaded with an active substance. The ratio q of the external diameter $r_a$ of the hollow body to the internal diameter $r_i$ of the hollow body is about 1.2 to 3.0.

29 Claims, 3 Drawing Sheets

(56) References Cited

U.S. PATENT DOCUMENTS

| | | |
|---|---|---|
| 3,910,617 A | 10/1975 | Scalza et al. |
| 3,921,636 A | 11/1975 | Zaffaroni |
| 3,948,254 A | 4/1976 | Zaffaroni |
| 3,948,262 A | 4/1976 | Zaffaroni |
| 3,967,618 A | 7/1976 | Zaffaroni |
| 3,993,069 A | 11/1976 | Buckles et al. |
| 3,993,072 A | 11/1976 | Zaffaroni |
| 3,993,073 A | 11/1976 | Zaffaroni |
| 4,016,251 A | 4/1977 | Higuchi et al. |
| 4,052,505 A | 10/1977 | Higuchi et al. |
| 4,053,975 A | 10/1977 | Olbrich et al. |
| 4,069,307 A | 1/1978 | Higuchi et al. |
| 4,102,342 A | 7/1978 | Akiyama et al. |
| 4,138,151 A | 2/1979 | Nakao |
| 4,184,497 A | 1/1980 | Kolff et al. |
| 4,198,766 A | 4/1980 | Camin et al. |
| 4,207,890 A | 6/1980 | Mamajek et al. |
| 4,209,919 A | 7/1980 | Kirikae et al. |
| 4,213,095 A | 7/1980 | Falconer |
| 4,217,898 A | 8/1980 | Theeuwes |
| 4,249,531 A | 2/1981 | Heller et al. |
| 4,268,115 A | 5/1981 | Slemon et al. |
| 4,299,226 A | 11/1981 | Banka |
| 4,299,227 A | 11/1981 | Lincoff |
| 4,312,353 A | 1/1982 | Shahbabian |
| 4,338,941 A | 7/1982 | Payton |
| D269,204 S | 5/1983 | Trepp |
| 4,388,941 A | 6/1983 | Riedhammer |
| RE31,351 E | 8/1983 | Falconer |
| 4,435,716 A | 3/1984 | Zandbergen |
| 4,437,856 A | 3/1984 | Valli |
| 4,450,150 A * | 5/1984 | Sidman ................ 424/424 |
| 4,459,977 A | 7/1984 | Pizon et al. |
| 4,464,175 A | 8/1984 | Altman et al. |
| 4,471,779 A | 9/1984 | Antoshkiw et al. |
| 4,499,899 A | 2/1985 | Lyons, III |
| 4,554,929 A | 11/1985 | Samson et al. |
| 4,564,364 A * | 1/1986 | Zaffaroni et al. ........ 424/484 |
| 4,571,239 A | 2/1986 | Heyman |
| 4,571,240 A | 2/1986 | Samson et al. |
| 4,581,017 A | 4/1986 | Sahota |
| 4,585,000 A | 4/1986 | Hershenson |
| D283,921 S | 5/1986 | Dyak |
| 4,589,868 A | 5/1986 | Dretler |
| 4,596,528 A | 6/1986 | Lewis et al. |
| D284,892 S | 7/1986 | Glassman |
| 4,603,564 A | 8/1986 | Kleinhany et al. |
| 4,606,346 A | 8/1986 | Berg et al. |
| 4,607,622 A | 8/1986 | Fritch et al. |
| 4,637,389 A | 1/1987 | Heyden |
| 4,639,244 A | 1/1987 | Rizk et al. |
| 4,645,495 A | 2/1987 | Vaillancourt |
| 4,669,469 A | 6/1987 | Gifford, III |
| 4,672,961 A | 6/1987 | Davies |
| 4,675,613 A | 6/1987 | Naegeli et al. |
| 4,691,948 A | 9/1987 | Austin, Jr. et al. |
| 4,708,434 A | 11/1987 | Tsuno |
| 4,708,834 A | 11/1987 | Cohen et al. |
| 4,726,772 A | 2/1988 | Amplatz |
| 4,736,970 A | 4/1988 | McGourty et al. |
| 4,737,141 A | 4/1988 | Spits |
| 4,748,869 A | 6/1988 | Ohtsuka |
| 4,748,969 A | 6/1988 | Wardle |
| 4,748,986 A | 6/1988 | Morrison et al. |
| 4,755,171 A * | 7/1988 | Tennant ................ 604/265 |
| 4,771,776 A | 9/1988 | Powell et al. |
| 4,793,359 A | 12/1988 | Sharrow |
| 4,795,439 A | 1/1989 | Guest |
| 4,796,629 A | 1/1989 | Grayzel |
| 4,803,076 A | 2/1989 | Ranade |
| 4,811,743 A | 3/1989 | Stevens |
| 4,815,478 A | 3/1989 | Buchbinder et al. |
| 4,819,619 A | 4/1989 | Augustine et al. |
| 4,846,186 A | 7/1989 | Box et al. |
| 4,847,258 A | 7/1989 | Sturm et al. |
| 4,851,228 A | 7/1989 | Zentner et al. |
| 4,854,330 A | 8/1989 | Evans, III et al. |
| 4,862,874 A | 9/1989 | Kellner |
| 4,867,138 A | 9/1989 | Kubota et al. |
| 4,883,465 A | 11/1989 | Brennan |
| 4,897,651 A | 1/1990 | DeMonte |
| 4,898,577 A | 2/1990 | Badger et al. |
| 4,917,419 A | 4/1990 | Mora, Jr. et al. |
| 4,917,667 A | 4/1990 | Jackson |
| 4,919,112 A | 4/1990 | Siegmund |
| 4,920,967 A | 5/1990 | Cottonaro et al. |
| 4,925,445 A | 5/1990 | Sakamoto et al. |
| 4,940,062 A | 7/1990 | Hampton et al. |
| 4,943,275 A | 7/1990 | Stricker |
| 4,946,466 A | 8/1990 | Pinchuk et al. |
| 4,961,433 A | 10/1990 | Christian |
| 4,966,163 A | 10/1990 | Kraus et al. |
| 4,984,581 A | 1/1991 | Stice |
| 4,994,033 A | 2/1991 | Shockey et al. |
| 4,998,916 A | 3/1991 | Hammerslag et al. |
| 4,998,917 A | 3/1991 | Gaiser et al. |
| 5,001,825 A | 3/1991 | Halpern |
| 5,002,322 A | 3/1991 | Fukumoto |
| 5,019,075 A | 5/1991 | Spears et al. |
| 5,019,372 A | 5/1991 | Folkman et al. |
| 5,020,514 A | 6/1991 | Heckele |
| 5,021,043 A | 6/1991 | Becker et al. |
| 5,024,650 A | 6/1991 | Hagiwara et al. |
| 5,024,658 A | 6/1991 | Kozlov et al. |
| 5,026,384 A | 6/1991 | Farr et al. |
| 5,030,227 A | 7/1991 | Rosenbluth et al. |
| 5,041,089 A | 8/1991 | Mueller et al. |
| 5,044,678 A | 9/1991 | Detweiler |
| 5,053,007 A | 10/1991 | Euteneuer |
| 5,055,051 A | 10/1991 | Duncan |
| 5,060,660 A | 10/1991 | Gambale et al. |
| 5,067,489 A | 11/1991 | Lind |
| 5,069,226 A | 12/1991 | Yamauchi et al. |
| 5,087,244 A | 2/1992 | Wolinsky et al. |
| 5,087,246 A | 2/1992 | Smith |
| 5,090,595 A | 2/1992 | Vandoninck |
| 5,090,910 A | 2/1992 | Narlo |
| 5,112,228 A | 5/1992 | Zouras |
| 5,116,311 A | 5/1992 | Lofstedt |
| 5,127,393 A | 7/1992 | McFarlin et al. |
| 5,137,517 A | 8/1992 | Loney et al. |
| 5,139,510 A | 8/1992 | Goldsmith, III et al. |
| 5,139,832 A | 8/1992 | Hayashi et al. |
| D329,496 S | 9/1992 | Wotton |
| 5,152,747 A | 10/1992 | Olivier |
| 5,156,595 A | 10/1992 | Adams |
| 5,163,989 A | 11/1992 | Campbell et al. |
| 5,167,220 A | 12/1992 | Brown |
| 5,168,864 A | 12/1992 | Shockey |
| 5,169,043 A | 12/1992 | Catania |
| 5,169,386 A | 12/1992 | Becker et al. |
| 5,171,233 A | 12/1992 | Amplatz et al. |
| 5,180,368 A | 1/1993 | Garrison |
| 5,183,470 A | 2/1993 | Wettermann |
| 5,189,110 A * | 2/1993 | Ikematu et al. ............... 525/314 |
| 5,195,168 A | 3/1993 | Yong |
| 5,197,457 A | 3/1993 | Adair |
| 5,207,695 A | 5/1993 | Trout, III |
| 5,211,952 A * | 5/1993 | Spicer et al. ................ 424/426 |
| 5,215,105 A | 6/1993 | Kizelshteyn et al. |
| 5,221,260 A | 6/1993 | Burns et al. |
| 5,226,302 A | 7/1993 | Anderson |
| 5,230,348 A | 7/1993 | Ishibe et al. |
| 5,236,422 A | 8/1993 | Eplett, Jr. |
| 5,243,996 A | 9/1993 | Hall |
| D340,111 S | 10/1993 | Yoshikawa |
| 5,250,059 A | 10/1993 | Andreas et al. |
| 5,251,092 A | 10/1993 | Brady et al. |
| 5,252,183 A | 10/1993 | Shaban et al. |
| 5,255,679 A | 10/1993 | Imran |
| 5,256,144 A | 10/1993 | Kraus et al. |
| 5,263,926 A | 11/1993 | Wilk |
| 5,264,260 A | 11/1993 | Saab |
| 5,267,965 A | 12/1993 | Deniega |

(56) References Cited

U.S. PATENT DOCUMENTS

| | | |
|---|---|---|
| 5,270,086 A | 12/1993 | Hamlin |
| 5,273,052 A | 12/1993 | Kraus et al. |
| 5,275,593 A | 1/1994 | Easley et al. |
| 5,286,254 A | 2/1994 | Shapland et al. |
| 5,290,310 A | 3/1994 | Makower et al. |
| 5,295,694 A | 3/1994 | Levin |
| 5,300,085 A | 4/1994 | Yock |
| 5,304,123 A | 4/1994 | Atala et al. |
| 5,308,326 A | 5/1994 | Zimmon |
| 5,313,967 A | 5/1994 | Lieber et al. |
| 5,314,417 A | 5/1994 | Stephens et al. |
| 5,315,618 A | 5/1994 | Yoshida |
| 5,324,306 A | 6/1994 | Makower et al. |
| 5,333,620 A | 8/1994 | Moutafis et al. |
| 5,334,167 A | 8/1994 | Cocanower |
| 5,336,163 A | 8/1994 | DeMane et al. |
| 5,341,818 A | 8/1994 | Abrams et al. |
| 5,342,296 A | 8/1994 | Persson et al. |
| 5,343,865 A | 9/1994 | Gardineer et al. |
| 5,345,945 A | 9/1994 | Hodgson et al. |
| 5,346,075 A | 9/1994 | Nichols et al. |
| 5,346,508 A | 9/1994 | Hastings |
| 5,348,537 A | 9/1994 | Wiesner et al. |
| 5,350,396 A | 9/1994 | Eliachar |
| 5,356,418 A | 10/1994 | Shturman |
| 5,368,049 A | 11/1994 | Raman et al. |
| 5,368,558 A | 11/1994 | Nita |
| 5,368,566 A | 11/1994 | Crocker |
| 5,372,138 A | 12/1994 | Crowley et al. |
| 5,372,584 A | 12/1994 | Zink et al. |
| D355,031 S | 1/1995 | Yoshikawa |
| 5,386,817 A | 2/1995 | Jones |
| 5,391,147 A | 2/1995 | Imran et al. |
| 5,391,179 A | 2/1995 | Mezzoli |
| 5,402,799 A | 4/1995 | Colon et al. |
| 5,409,444 A | 4/1995 | Kensey |
| 5,411,475 A | 5/1995 | Atala et al. |
| 5,411,476 A | 5/1995 | Abrams et al. |
| 5,411,477 A | 5/1995 | Saab |
| 5,415,633 A | 5/1995 | Lazarus |
| 5,425,370 A | 6/1995 | Vilkomerson |
| 5,439,446 A | 8/1995 | Barry |
| 5,441,494 A | 8/1995 | Ortiz |
| 5,441,497 A | 8/1995 | Narciso, Jr. |
| 5,443,458 A | 8/1995 | Eury |
| 5,450,853 A | 9/1995 | Hastings et al. |
| 5,451,221 A | 9/1995 | Cho et al. |
| 5,454,817 A | 10/1995 | Katz |
| 5,458,572 A | 10/1995 | Campbell et al. |
| 5,465,717 A | 11/1995 | Imran et al. |
| 5,465,733 A | 11/1995 | Hinohara et al. |
| 5,478,565 A | 12/1995 | Geria |
| 5,486,181 A | 1/1996 | Cohen et al. |
| 5,496,338 A | 3/1996 | Miyagi et al. |
| 5,497,783 A | 3/1996 | Urick et al. |
| 5,507,301 A | 4/1996 | Wasicek et al. |
| 5,507,725 A | 4/1996 | Savage et al. |
| 5,507,766 A | 4/1996 | Kugo et al. |
| 5,512,055 A | 4/1996 | Domb et al. |
| 5,514,128 A | 5/1996 | Hillsman et al. |
| 5,519,532 A | 5/1996 | Broome |
| 5,531,676 A | 7/1996 | Edwards et al. |
| 5,533,985 A | 7/1996 | Wong |
| 5,538,008 A | 7/1996 | Crowe |
| 5,546,964 A | 8/1996 | Stangerup |
| 5,549,542 A | 8/1996 | Kovalcheck |
| 5,558,073 A | 9/1996 | Pomeranz et al. |
| 5,558,652 A | 9/1996 | Henke |
| 5,562,619 A | 10/1996 | Mirarchi et al. |
| 5,568,809 A | 10/1996 | Ben-Haim |
| 5,571,086 A | 11/1996 | Kaplan et al. |
| 5,578,007 A | 11/1996 | Imran |
| 5,578,048 A | 11/1996 | Pasqualucci et al. |
| 5,584,827 A | 12/1996 | Korteweg et al. |
| 5,591,194 A | 1/1997 | Berthiaume |
| 5,599,284 A | 2/1997 | Shea |
| 5,599,304 A | 2/1997 | Shaari |
| 5,599,576 A | 2/1997 | Opolski |
| 5,601,087 A | 2/1997 | Gunderson et al. |
| 5,601,594 A | 2/1997 | Best |
| 5,607,386 A | 3/1997 | Flam |
| 5,617,870 A | 4/1997 | Hastings et al. |
| 5,626,374 A | 5/1997 | Kim |
| 5,633,000 A | 5/1997 | Grossman et al. |
| 5,634,908 A | 6/1997 | Loomas |
| 5,638,819 A | 6/1997 | Manwaring et al. |
| 5,643,251 A | 7/1997 | Hillsman et al. |
| 5,645,789 A | 7/1997 | Roucher, Jr. |
| 5,647,361 A | 7/1997 | Damadian |
| 5,656,030 A | 8/1997 | Hunjan et al. |
| 5,662,674 A | 9/1997 | Debbas |
| 5,664,567 A | 9/1997 | Linder |
| 5,664,580 A | 9/1997 | Erickson et al. |
| 5,665,052 A | 9/1997 | Bullard |
| 5,669,388 A | 9/1997 | Vilkomerson |
| 5,673,707 A | 10/1997 | Chandrasekaran |
| 5,676,673 A | 10/1997 | Ferre et al. |
| 5,679,400 A | 10/1997 | Tuch |
| 5,682,199 A | 10/1997 | Lankford |
| 5,685,838 A | 11/1997 | Peters et al. |
| 5,685,847 A | 11/1997 | Barry |
| 5,690,373 A | 11/1997 | Luker |
| 5,693,065 A * | 12/1997 | Rains, III .................. 606/184 |
| 5,694,945 A | 12/1997 | Ben-Haim |
| 5,697,159 A | 12/1997 | Linden |
| 5,697,400 A | 12/1997 | Pfeifer |
| 5,700,286 A | 12/1997 | Tartaglia et al. |
| 5,707,389 A | 1/1998 | Louw et al. |
| 5,708,175 A | 1/1998 | Koyanagi et al. |
| 5,711,315 A | 1/1998 | Jerusalmy |
| 5,713,839 A | 2/1998 | Shea |
| 5,713,946 A | 2/1998 | Ben-Haim |
| 5,718,702 A | 2/1998 | Edwards |
| 5,720,300 A | 2/1998 | Fagan et al. |
| 5,722,401 A | 3/1998 | Pietroski et al. |
| 5,722,984 A | 3/1998 | Fischell et al. |
| 5,729,129 A | 3/1998 | Acker |
| 5,730,128 A | 3/1998 | Pomeranz et al. |
| 5,733,248 A | 3/1998 | Adams et al. |
| 5,741,333 A | 4/1998 | Frid |
| 5,752,513 A | 5/1998 | Acker et al. |
| 5,762,604 A | 6/1998 | Kieturakis |
| 5,766,158 A | 6/1998 | Opolski |
| 5,775,327 A | 7/1998 | Randolph et al. |
| 5,776,158 A | 7/1998 | Chou |
| 5,779,699 A | 7/1998 | Lipson |
| 5,789,391 A | 8/1998 | Jacobus et al. |
| 5,792,100 A | 8/1998 | Shantha |
| 5,797,878 A | 8/1998 | Bleam |
| 5,803,089 A | 9/1998 | Ferre et al. |
| 5,814,016 A | 9/1998 | Valley et al. |
| 5,819,723 A | 10/1998 | Joseph |
| 5,820,568 A | 10/1998 | Willis |
| 5,824,044 A | 10/1998 | Quiachon et al. |
| 5,824,048 A | 10/1998 | Tuch |
| 5,824,173 A | 10/1998 | Fontirroche et al. |
| 5,827,224 A | 10/1998 | Shippert |
| 5,830,188 A | 11/1998 | Abouleish |
| 5,833,608 A | 11/1998 | Acker |
| 5,833,645 A | 11/1998 | Lieber et al. |
| 5,833,650 A | 11/1998 | Imran |
| 5,833,682 A | 11/1998 | Amplatz et al. |
| 5,836,638 A | 11/1998 | Slocum |
| 5,836,935 A | 11/1998 | Ashton et al. |
| 5,837,313 A | 11/1998 | Ding et al. |
| 5,843,089 A | 12/1998 | Sahatjian et al. |
| 5,843,113 A | 12/1998 | High |
| 5,846,259 A | 12/1998 | Berthiaume |
| 5,857,998 A | 1/1999 | Barry |
| 5,862,693 A | 1/1999 | Myers et al. |
| 5,865,767 A | 2/1999 | Frechette et al. |
| 5,872,879 A | 2/1999 | Hamm |
| 5,873,835 A | 2/1999 | Hastings |
| 5,887,467 A | 3/1999 | Butterwreck et al. |

(56) References Cited

U.S. PATENT DOCUMENTS

| | | |
|---|---|---|
| 5,902,247 A | 5/1999 | Coe et al. |
| 5,902,333 A | 5/1999 | Roberts et al. |
| 5,904,701 A | 5/1999 | Daneshvar |
| 5,908,407 A | 6/1999 | Frazee et al. |
| 5,916,193 A | 6/1999 | Stevens et al. |
| 5,928,192 A | 7/1999 | Maahs |
| 5,931,811 A | 8/1999 | Haissaguerre et al. |
| 5,931,818 A | 8/1999 | Werp et al. |
| 5,932,035 A | 8/1999 | Koger et al. |
| 5,935,061 A | 8/1999 | Acker et al. |
| 5,941,816 A | 8/1999 | Barthel et al. |
| D413,629 S | 9/1999 | Wolff et al. |
| 5,947,988 A | 9/1999 | Smith |
| 5,949,929 A | 9/1999 | Hamm |
| 5,954,693 A | 9/1999 | Barry |
| 5,954,694 A | 9/1999 | Sunseri |
| 5,957,842 A | 9/1999 | Littmann et al. |
| 5,968,085 A | 10/1999 | Morris et al. |
| 5,971,975 A | 10/1999 | Mills et al. |
| 5,979,290 A | 11/1999 | Simeone |
| 5,980,503 A | 11/1999 | Chin |
| 5,980,551 A | 11/1999 | Summers et al. |
| 5,984,945 A | 11/1999 | Sirhan |
| 5,985,307 A | 11/1999 | Hanson et al. |
| 5,997,562 A | 12/1999 | Zadno-Azizi |
| 6,006,126 A | 12/1999 | Cosman |
| 6,006,130 A | 12/1999 | Higo et al. |
| 6,007,516 A | 12/1999 | Burbank et al. |
| 6,007,991 A * | 12/1999 | Sivaraman et al. ............. 435/6 |
| 6,010,511 A | 1/2000 | Murphy |
| 6,013,019 A | 1/2000 | Fischell et al. |
| 6,015,414 A | 1/2000 | Werp et al. |
| 6,016,429 A | 1/2000 | Khafizov et al. |
| 6,016,439 A | 1/2000 | Acker |
| 6,019,736 A | 2/2000 | Avellanet et al. |
| 6,019,777 A | 2/2000 | Mackenzie |
| 6,021,340 A | 2/2000 | Randolph et al. |
| 6,022,313 A | 2/2000 | Ginn et al. |
| 6,027,461 A | 2/2000 | Walker et al. |
| 6,027,478 A | 2/2000 | Katz |
| 6,039,699 A | 3/2000 | Viera |
| 6,042,561 A | 3/2000 | Ash et al. |
| 6,048,299 A | 4/2000 | Hoffmann |
| 6,048,358 A | 4/2000 | Barak |
| 6,053,172 A | 4/2000 | Hovda et al. |
| 6,056,702 A | 5/2000 | Lorenzo |
| 6,059,752 A | 5/2000 | Segal |
| 6,071,233 A | 6/2000 | Ishikawa et al. |
| 6,079,755 A | 6/2000 | Chang |
| 6,080,190 A | 6/2000 | Schwartz |
| 6,083,148 A | 7/2000 | Williams |
| 6,083,188 A | 7/2000 | Becker et al. |
| 6,086,585 A | 7/2000 | Hovda et al. |
| 6,092,846 A | 7/2000 | Fuss et al. |
| 6,093,150 A | 7/2000 | Chandler et al. |
| 6,093,195 A | 7/2000 | Ouchi |
| 6,109,268 A | 8/2000 | Thapliyal et al. |
| 6,113,567 A | 9/2000 | Becker |
| 6,117,105 A | 9/2000 | Bresnaham et al. |
| 6,122,541 A | 9/2000 | Cosman et al. |
| 6,123,697 A | 9/2000 | Shippert |
| 6,136,006 A | 10/2000 | Johnson et al. |
| 6,139,510 A | 10/2000 | Palermo |
| 6,142,957 A | 11/2000 | Diamond et al. |
| 6,148,823 A | 11/2000 | Hastings |
| 6,149,213 A | 11/2000 | Sokurenko et al. |
| 6,159,170 A | 12/2000 | Borodulin et al. |
| 6,171,298 B1 | 1/2001 | Matsuura et al. |
| 6,171,303 B1 | 1/2001 | Ben-Haim |
| 6,174,280 B1 | 1/2001 | Oneda et al. |
| 6,176,829 B1 | 1/2001 | Vilkomerson |
| 6,179,788 B1 | 1/2001 | Sullivan |
| 6,179,811 B1 | 1/2001 | Fugoso et al. |
| 6,183,461 B1 | 2/2001 | Matsuura et al. |
| 6,183,464 B1 | 2/2001 | Sharp et al. |
| 6,190,353 B1 | 2/2001 | Makower et al. |
| 6,190,381 B1 | 2/2001 | Olsen et al. |
| 6,193,650 B1 | 2/2001 | Ryan, Jr. |
| 6,195,225 B1 | 2/2001 | Komatsu et al. |
| 6,200,257 B1 | 3/2001 | Winkler |
| 6,206,870 B1 | 3/2001 | Kanner |
| 6,213,975 B1 | 4/2001 | Laksin |
| 6,221,042 B1 | 4/2001 | Adams |
| 6,231,543 B1 | 5/2001 | Hegde et al. |
| 6,234,958 B1 | 5/2001 | Snoke et al. |
| 6,238,364 B1 | 5/2001 | Becker |
| 6,238,391 B1 | 5/2001 | Olsen et al. |
| 6,241,519 B1 | 6/2001 | Sedelemayer |
| 6,249,180 B1 | 6/2001 | Maalej et al. |
| 6,254,550 B1 | 7/2001 | McNamara et al. |
| 6,268,574 B1 | 7/2001 | Edens |
| 6,293,957 B1 | 9/2001 | Peters et al. |
| 6,302,875 B1 | 10/2001 | Makower et al. |
| 6,306,105 B1 | 10/2001 | Rooney et al. |
| 6,306,124 B1 | 10/2001 | Jones et al. |
| D450,382 S | 11/2001 | Nestenborg |
| 6,322,495 B1 | 11/2001 | Snow et al. |
| 6,328,564 B1 | 12/2001 | Thurow |
| 6,332,089 B1 | 12/2001 | Acker et al. |
| 6,332,891 B1 | 12/2001 | Himes |
| 6,340,360 B1 | 1/2002 | Lyles et al. |
| 6,348,041 B1 | 2/2002 | Klint |
| 6,352,503 B1 | 3/2002 | Matsui et al. |
| 6,375,615 B1 | 4/2002 | Flaherty et al. |
| 6,375,629 B1 | 4/2002 | Muni et al. |
| 6,383,146 B1 | 5/2002 | Klint |
| 6,386,197 B1 | 5/2002 | Miller |
| 6,389,313 B1 | 5/2002 | Marchitto et al. |
| 6,390,993 B1 | 5/2002 | Cornish et al. |
| 6,394,093 B1 | 5/2002 | Lethi |
| 6,398,758 B1 | 6/2002 | Jacobsen et al. |
| 6,409,863 B1 | 6/2002 | Williams et al. |
| 6,423,012 B1 | 7/2002 | Kato et al. |
| 6,425,877 B1 | 7/2002 | Edwards |
| 6,432,986 B2 | 8/2002 | Levin |
| 6,440,061 B1 | 8/2002 | Wenner et al. |
| 6,443,947 B1 | 9/2002 | Marko et al. |
| 6,445,939 B1 | 9/2002 | Swanson et al. |
| 6,450,975 B1 | 9/2002 | Brennan et al. |
| 6,450,989 B2 | 9/2002 | Dubrul et al. |
| 6,464,650 B2 | 10/2002 | Jafari et al. |
| 6,468,202 B1 | 10/2002 | Irion et al. |
| 6,468,297 B1 | 10/2002 | Williams et al. |
| 6,485,475 B1 | 11/2002 | Chelly |
| 6,491,940 B1 | 12/2002 | Levin |
| 6,494,894 B2 | 12/2002 | Mirarchi |
| 6,500,130 B2 | 12/2002 | Kinsella et al. |
| 6,500,189 B1 | 12/2002 | Lang et al. |
| 6,503,087 B1 | 1/2003 | Eggert et al. |
| 6,503,185 B1 | 1/2003 | Waksman et al. |
| 6,511,418 B2 | 1/2003 | Shahidi et al. |
| 6,514,249 B1 | 2/2003 | Maguire et al. |
| 6,517,478 B2 | 2/2003 | Khadem |
| 6,524,299 B1 | 2/2003 | Tran et al. |
| 6,526,302 B2 | 2/2003 | Hassett |
| 6,527,753 B2 | 3/2003 | Sekine et al. |
| 6,529,756 B1 | 3/2003 | Phan et al. |
| 6,533,754 B1 | 3/2003 | Hisamatsu et al. |
| 6,536,437 B1 | 3/2003 | Dragisic |
| 6,537,294 B1 | 3/2003 | Boyle et al. |
| 6,543,452 B1 | 4/2003 | Lavigne |
| 6,544,230 B1 | 4/2003 | Flaherty et al. |
| 6,549,800 B1 | 4/2003 | Atalar et al. |
| 6,551,239 B2 | 4/2003 | Renner et al. |
| 6,569,146 B1 | 5/2003 | Werner et al. |
| 6,569,147 B1 | 5/2003 | Evans et al. |
| 6,571,131 B1 | 5/2003 | Nguyen |
| 6,572,538 B2 | 6/2003 | Takase |
| 6,572,590 B1 | 6/2003 | Stevens et al. |
| 6,579,285 B2 | 6/2003 | Sinofsky |
| 6,585,639 B1 | 7/2003 | Kotmel et al. |
| 6,585,717 B1 | 7/2003 | Wittenberger et al. |
| 6,585,794 B2 | 7/2003 | Shimoda et al. |
| 6,596,009 B1 | 7/2003 | Jelic |

(56) References Cited

U.S. PATENT DOCUMENTS

| | | |
|---|---|---|
| 6,607,546 B1 | 8/2003 | Murken |
| 6,613,066 B1 | 9/2003 | Fukaya et al. |
| 6,616,601 B2 | 9/2003 | Hayakawa |
| 6,616,659 B1 | 9/2003 | de la Torre et al. |
| 6,616,678 B2 | 9/2003 | Nishtala et al. |
| 6,616,913 B1 | 9/2003 | Mautone |
| 6,619,085 B1 | 9/2003 | Hsieh |
| 6,634,684 B2 | 10/2003 | Spiessl |
| 6,638,233 B2 | 10/2003 | Corvi et al. |
| 6,638,268 B2 | 10/2003 | Niazi |
| 6,638,291 B1 | 10/2003 | Ferrera et al. |
| 6,652,472 B2 | 11/2003 | Jafari et al. |
| 6,652,480 B1 | 11/2003 | Imran et al. |
| 6,652,575 B2 | 11/2003 | Wang |
| 6,663,589 B1 | 12/2003 | Halevy |
| 6,669,689 B2 | 12/2003 | Lehmann et al. |
| 6,669,711 B1 | 12/2003 | Noda |
| 6,672,773 B1 | 1/2004 | Glenn et al. |
| 6,673,025 B1 | 1/2004 | Richardson et al. |
| 6,685,648 B2 | 2/2004 | Flaherty et al. |
| 6,689,096 B1 | 2/2004 | Loubens et al. |
| 6,689,146 B1 | 2/2004 | Himes |
| 6,702,735 B2 | 3/2004 | Kelly |
| 6,712,757 B2 | 3/2004 | Becker et al. |
| 6,714,809 B2 | 3/2004 | Lee et al. |
| 6,716,216 B1 | 4/2004 | Boucher et al. |
| 6,716,813 B2 | 4/2004 | Lim et al. |
| 6,719,749 B1 | 4/2004 | Schweikert et al. |
| 6,755,812 B2 | 6/2004 | Peterson et al. |
| 6,776,772 B1 | 8/2004 | Vrijer et al. |
| 6,780,168 B2 | 8/2004 | Jellie |
| 6,783,522 B2 | 8/2004 | Fischell |
| 6,783,536 B2 | 8/2004 | Vilsmeier et al. |
| 6,786,864 B2 | 9/2004 | Matsuura et al. |
| 6,796,960 B2 | 9/2004 | Cioanta et al. |
| 6,817,976 B2 | 11/2004 | Rovengo |
| 6,832,715 B2 | 12/2004 | Eungard et al. |
| D501,677 S | 2/2005 | Becker |
| 6,851,290 B1 | 2/2005 | Meier et al. |
| 6,860,264 B2 | 3/2005 | Christopher |
| 6,860,849 B2 | 3/2005 | Matsushita et al. |
| 6,878,106 B1 | 4/2005 | Herrmann |
| 6,890,329 B2 | 5/2005 | Carroll et al. |
| 6,899,672 B2 | 5/2005 | Chin et al. |
| 6,902,556 B2 | 6/2005 | Grimes et al. |
| 6,927,478 B2 | 8/2005 | Paek |
| 6,939,361 B1 | 9/2005 | Kleshinski |
| 6,955,657 B1 | 10/2005 | Webler |
| 6,966,906 B2 | 11/2005 | Brown |
| 6,979,290 B2 | 12/2005 | Mourlas et al. |
| 6,991,597 B2 * | 1/2006 | Gellman et al. ........... 600/37 |
| 6,997,931 B2 | 2/2006 | Sauer et al. |
| 6,997,941 B2 | 2/2006 | Sharkey et al. |
| 7,011,654 B2 | 3/2006 | Dubrul et al. |
| 7,022,105 B1 | 4/2006 | Edwards |
| 7,043,961 B2 | 5/2006 | Pandey |
| 7,052,474 B2 | 5/2006 | Castell et al. |
| 7,056,284 B2 | 6/2006 | Martone et al. |
| 7,056,303 B2 | 6/2006 | Dennis et al. |
| 7,074,197 B2 | 7/2006 | Reynolds et al. |
| 7,074,426 B2 | 7/2006 | Kochinke |
| 7,097,612 B2 | 8/2006 | Bertolero et al. |
| 7,108,706 B2 | 9/2006 | Hogle |
| 7,128,718 B2 | 10/2006 | Hojeibane et al. |
| 7,131,969 B1 | 11/2006 | Hovda et al. |
| 7,140,480 B2 | 11/2006 | Drussel et al. |
| D534,216 S | 12/2006 | Makower et al. |
| 7,160,255 B2 | 1/2007 | Saadat |
| 7,169,140 B1 | 1/2007 | Kume |
| 7,169,163 B2 | 1/2007 | Becker |
| 7,172,562 B2 | 2/2007 | McKinley |
| 7,174,774 B2 | 2/2007 | Pawar et al. |
| 7,182,735 B2 | 2/2007 | Shireman et al. |
| 7,184,827 B1 | 2/2007 | Edwards |
| 7,233,820 B2 | 6/2007 | Gilboa |
| 7,235,099 B1 | 6/2007 | Duncavage et al. |
| 7,237,313 B2 | 7/2007 | Skujins et al. |
| 7,252,677 B2 | 8/2007 | Burwell et al. |
| 7,282,057 B2 | 10/2007 | Surti et al. |
| 7,294,345 B2 | 11/2007 | Haapakumpu et al. |
| 7,294,365 B2 | 11/2007 | Hayakawa et al. |
| 7,316,168 B2 | 1/2008 | van der Knokke et al. |
| 7,318,831 B2 | 1/2008 | Alvarez et al. |
| 7,322,934 B2 | 1/2008 | Miyake et al. |
| 7,326,235 B2 | 2/2008 | Edwards |
| 7,338,467 B2 | 3/2008 | Lutter |
| 7,361,168 B2 | 4/2008 | Makower et al. |
| 7,366,562 B2 | 4/2008 | Dukesherer |
| 7,371,210 B2 | 5/2008 | Brock et al. |
| 7,381,205 B2 | 6/2008 | Thommen |
| 7,410,480 B2 | 8/2008 | Muni et al. |
| 7,419,497 B2 | 9/2008 | Muni et al. |
| 7,442,191 B2 | 10/2008 | Hovda et al. |
| 7,452,351 B2 | 11/2008 | Miller et al. |
| 7,454,244 B2 | 11/2008 | Kassab et al. |
| 7,462,175 B2 | 12/2008 | Chang et al. |
| D586,465 S | 2/2009 | Faulkner et al. |
| D586,916 S | 2/2009 | Faulkner et al. |
| 7,488,313 B2 | 2/2009 | Segal et al. |
| 7,493,156 B2 | 2/2009 | Manning et al. |
| 7,500,971 B2 | 3/2009 | Chang et al. |
| D590,502 S | 4/2009 | Geisser et al. |
| 7,520,876 B2 | 4/2009 | Ressemann et al. |
| 7,532,920 B1 | 5/2009 | Ainsworth et al. |
| 7,559,925 B2 | 7/2009 | Goldfarb et al. |
| 7,625,335 B2 | 12/2009 | Deichmann et al. |
| 7,641,668 B2 | 1/2010 | Perry et al. |
| 7,645,272 B2 | 1/2010 | Chang et al. |
| 7,648,367 B1 | 1/2010 | Makower et al. |
| 7,654,997 B2 | 2/2010 | Makower et al. |
| 7,717,933 B2 | 5/2010 | Becker |
| 7,720,521 B2 | 5/2010 | Chang et al. |
| 7,736,301 B1 | 6/2010 | Webler et al. |
| 7,740,642 B2 | 6/2010 | Becker |
| 7,753,929 B2 | 7/2010 | Becker |
| 7,799,048 B2 | 9/2010 | Hudson et al. |
| 7,803,150 B2 | 9/2010 | Chang et al. |
| 7,837,672 B2 | 11/2010 | Intoccia |
| D630,321 S | 1/2011 | Hamilton, Jr. |
| D632,791 S | 2/2011 | Murner |
| 7,988,705 B2 | 8/2011 | Galdonik et al. |
| 8,123,722 B2 | 2/2012 | Chang et al. |
| 8,197,552 B2 | 6/2012 | Mandpe |
| 2001/0004644 A1 | 6/2001 | Levin |
| 2001/0016684 A1 | 8/2001 | Shahidi |
| 2001/0023332 A1 | 9/2001 | Hahnen |
| 2001/0027307 A1 | 10/2001 | Dubrul et al. |
| 2001/0029317 A1 | 10/2001 | Hayakawa |
| 2001/0034530 A1 | 10/2001 | Malackowski et al. |
| 2001/0051761 A1 | 12/2001 | Khadem |
| 2001/0051802 A1 | 12/2001 | Woloszko et al. |
| 2002/0002349 A1 | 1/2002 | Flaherty et al. |
| 2002/0006961 A1 * | 1/2002 | Katz et al. ........... 514/625 |
| 2002/0010384 A1 | 1/2002 | Shahidi et al. |
| 2002/0010426 A1 | 1/2002 | Clayman et al. |
| 2002/0016564 A1 | 2/2002 | Courtney et al. |
| 2002/0026155 A1 | 2/2002 | Mangosong |
| 2002/0029030 A1 | 3/2002 | Lurie et al. |
| 2002/0031941 A1 | 3/2002 | Cote et al. |
| 2002/0038130 A1 | 3/2002 | Adams |
| 2002/0055746 A1 | 5/2002 | Burke et al. |
| 2002/0062133 A1 | 5/2002 | Gilson et al. |
| 2002/0077852 A1 | 6/2002 | Ford et al. |
| 2002/0082558 A1 | 6/2002 | Samson et al. |
| 2002/0082583 A1 | 6/2002 | Lerner |
| 2002/0090388 A1 | 7/2002 | Humes et al. |
| 2002/0103459 A1 | 8/2002 | Sparks et al. |
| 2002/0107475 A1 | 8/2002 | Maginot |
| 2002/0116011 A1 | 8/2002 | Chee Chung et al. |
| 2002/0116043 A1 | 8/2002 | Garibaldi et al. |
| 2002/0165521 A1 | 11/2002 | Cioanta et al. |
| 2003/0013985 A1 | 1/2003 | Saadat |
| 2003/0014008 A1 | 1/2003 | Jacques |
| 2003/0014036 A1 | 1/2003 | Varner et al. |

(56) References Cited

U.S. PATENT DOCUMENTS

| | | |
|---|---|---|
| 2003/0017111 A1 | 1/2003 | Rabito |
| 2003/0018291 A1 | 1/2003 | Hill et al. |
| 2003/0032942 A1 | 2/2003 | Theeuwes et al. |
| 2003/0040697 A1 | 2/2003 | Pass et al. |
| 2003/0069521 A1 | 4/2003 | Reynolds et al. |
| 2003/0069549 A1 | 4/2003 | MacMahon et al. |
| 2003/0073955 A1 | 4/2003 | Otawara |
| 2003/0073972 A1 | 4/2003 | Rosenman et al. |
| 2003/0083608 A1 | 5/2003 | Evans et al. |
| 2003/0083613 A1 | 5/2003 | Schaer |
| 2003/0100886 A1 | 5/2003 | Segal et al. |
| 2003/0109810 A1 | 6/2003 | Brennan et al. |
| 2003/0114732 A1 | 6/2003 | Webler et al. |
| 2003/0120339 A1 | 6/2003 | Banik et al. |
| 2003/0130598 A1 | 7/2003 | Manning et al. |
| 2003/0163154 A1 | 8/2003 | Miyata et al. |
| 2003/0164952 A1 | 9/2003 | Deichmann et al. |
| 2003/0171650 A1 | 9/2003 | Tartaglia et al. |
| 2003/0181827 A1 | 9/2003 | Hojeibane et al. |
| 2003/0185872 A1 | 10/2003 | Kochinke |
| 2003/0208194 A1 | 11/2003 | Hovda et al. |
| 2003/0209096 A1 | 11/2003 | Pandey et al. |
| 2003/0212446 A1 | 11/2003 | Kaplan et al. |
| 2003/0225329 A1 | 12/2003 | Rossner et al. |
| 2004/0015150 A1 | 1/2004 | Zadno-Azizi |
| 2004/0018980 A1 | 1/2004 | Gurney et al. |
| 2004/0034311 A1 | 2/2004 | Mihalcik |
| 2004/0043052 A1 | 3/2004 | Hunter et al. |
| 2004/0058992 A1 | 3/2004 | Marinello et al. |
| 2004/0064083 A1 | 4/2004 | Becker |
| 2004/0064105 A1 | 4/2004 | Capes et al. |
| 2004/0064150 A1 | 4/2004 | Becker |
| 2004/0097788 A1 | 5/2004 | Mourlas et al. |
| 2004/0098017 A1 | 5/2004 | Saab et al. |
| 2004/0116958 A1 | 6/2004 | Gopferich et al. |
| 2004/0122471 A1 | 6/2004 | Toby et al. |
| 2004/0127820 A1 | 7/2004 | Clayman et al. |
| 2004/0158229 A1 | 8/2004 | Quinn |
| 2004/0167440 A1 | 8/2004 | Sharrow |
| 2004/0167442 A1 | 8/2004 | Shireman et al. |
| 2004/0167443 A1 | 8/2004 | Shireman et al. |
| 2004/0181175 A1 | 9/2004 | Clayman et al. |
| 2004/0193073 A1 | 9/2004 | DeMello et al. |
| 2004/0193139 A1 | 9/2004 | Armstrong et al. |
| 2004/0230095 A1 | 11/2004 | Stefanchik et al. |
| 2004/0230131 A1 | 11/2004 | Kassab et al. |
| 2004/0230156 A1 | 11/2004 | Schreck et al. |
| 2004/0236231 A1 | 11/2004 | Knighton et al. |
| 2004/0249243 A1 | 12/2004 | Kleiner |
| 2004/0249267 A1 | 12/2004 | Gilboa |
| 2004/0254625 A1 | 12/2004 | Stephens et al. |
| 2004/0267347 A1 | 12/2004 | Cervantes |
| 2005/0027249 A1 | 2/2005 | Reifart et al. |
| 2005/0043706 A1 | 2/2005 | Eaton et al. |
| 2005/0049486 A1 | 3/2005 | Urquhart et al. |
| 2005/0055077 A1 | 3/2005 | Marco et al. |
| 2005/0059931 A1 | 3/2005 | Garrison et al. |
| 2005/0089670 A1 | 4/2005 | Large et al. |
| 2005/0107720 A1 | 5/2005 | Burmeister et al. |
| 2005/0107738 A1 | 5/2005 | Slater et al. |
| 2005/0113686 A1 | 5/2005 | Peckham |
| 2005/0113687 A1 | 5/2005 | Herweck et al. |
| 2005/0113850 A1 | 5/2005 | Tagge |
| 2005/0119590 A1 | 6/2005 | Burmeister et al. |
| 2005/0124856 A1 | 6/2005 | Fujikura et al. |
| 2005/0131316 A1 | 6/2005 | Flagle et al. |
| 2005/0143687 A1 | 6/2005 | Rosenblatt et al. |
| 2005/0182319 A1 | 8/2005 | Glossop |
| 2005/0228260 A1 | 10/2005 | Burwell et al. |
| 2005/0228412 A1 | 10/2005 | Surti |
| 2005/0234507 A1 | 10/2005 | Geske et al. |
| 2005/0240147 A1 | 10/2005 | Makower et al. |
| 2005/0244472 A1 | 11/2005 | Hughes et al. |
| 2005/0245906 A1 | 11/2005 | Makower et al. |
| 2005/0273132 A1 | 12/2005 | Shluzas et al. |
| 2005/0283221 A1 | 12/2005 | Mann et al. |
| 2005/0288549 A1 | 12/2005 | Mathis |
| 2005/0288759 A1 | 12/2005 | Jones et al. |
| 2006/0004286 A1 | 1/2006 | Chang et al. |
| 2006/0004323 A1 | 1/2006 | Chang et al. |
| 2006/0063973 A1 | 3/2006 | Makower et al. |
| 2006/0067982 A1 | 3/2006 | Haapakumpu et al. |
| 2006/0074318 A1 | 4/2006 | Ahmed et al. |
| 2006/0085027 A1 | 4/2006 | Santin et al. |
| 2006/0095066 A1 | 5/2006 | Chang et al. |
| 2006/0106361 A1 | 5/2006 | Muni et al. |
| 2006/0107957 A1 | 5/2006 | Djupesland |
| 2006/0116749 A1 | 6/2006 | Willink et al. |
| 2006/0149310 A1 | 7/2006 | Becker |
| 2006/0161255 A1 | 7/2006 | Zarowski et al. |
| 2006/0173291 A1 | 8/2006 | Glossop |
| 2006/0173382 A1 | 8/2006 | Schreiner |
| 2006/0190022 A1 | 8/2006 | Beyar et al. |
| 2006/0210605 A1 | 9/2006 | Chang et al. |
| 2006/0211752 A1 | 9/2006 | Kohn et al. |
| 2006/0271024 A1 | 11/2006 | Gertner et al. |
| 2007/0005094 A1 | 1/2007 | Eaton et al. |
| 2007/0020196 A1 | 1/2007 | Pipkin et al. |
| 2007/0049929 A1 | 3/2007 | Catanese, III et al. |
| 2007/0073269 A1 | 3/2007 | Becker |
| 2007/0112358 A1 | 5/2007 | Abbott |
| 2007/0129751 A1 | 6/2007 | Muni et al. |
| 2007/0135789 A1 | 6/2007 | Chang et al. |
| 2007/0167682 A1 | 7/2007 | Goldfarb et al. |
| 2007/0207186 A1 | 9/2007 | Scanlon et al. |
| 2007/0208252 A1 | 9/2007 | Makower |
| 2007/0208301 A1 | 9/2007 | Evard et al. |
| 2007/0233036 A1 | 10/2007 | Madpe |
| 2007/0250105 A1 | 10/2007 | Ressemann et al. |
| 2007/0269385 A1 | 11/2007 | Yun et al. |
| 2007/0293727 A1 | 12/2007 | Goldfarb et al. |
| 2007/0293946 A1 | 12/2007 | Gonzales et al. |
| 2008/0015540 A1 | 1/2008 | Muni et al. |
| 2008/0015544 A1 | 1/2008 | Keith et al. |
| 2008/0033519 A1 | 2/2008 | Burwell et al. |
| 2008/0051804 A1 | 2/2008 | Cottler et al. |
| 2008/0082045 A1 | 4/2008 | Goldfarb et al. |
| 2008/0097154 A1 | 4/2008 | Makower et al. |
| 2008/0097239 A1 | 4/2008 | Chang et al. |
| 2008/0097295 A1 | 4/2008 | Makower et al. |
| 2008/0097400 A1 | 4/2008 | Chang et al. |
| 2008/0097514 A1 | 4/2008 | Chang et al. |
| 2008/0097515 A1 | 4/2008 | Chang et al. |
| 2008/0097516 A1 | 4/2008 | Chang et al. |
| 2008/0103361 A1 | 5/2008 | Makower et al. |
| 2008/0103521 A1 | 5/2008 | Makower et al. |
| 2008/0119693 A1 | 5/2008 | Makower et al. |
| 2008/0125046 A1 | 5/2008 | Deng et al. |
| 2008/0125626 A1 | 5/2008 | Chang et al. |
| 2008/0154250 A1 | 6/2008 | Makower et al. |
| 2008/0154345 A1 | 6/2008 | Taylor |
| 2008/0187098 A1 | 8/2008 | Gertner et al. |
| 2008/0188870 A1 | 8/2008 | Andre et al. |
| 2008/0195041 A1 | 8/2008 | Goldfarb et al. |
| 2008/0208242 A1 | 8/2008 | Becker |
| 2008/0208243 A1 | 8/2008 | Becker |
| 2008/0215082 A1 | 9/2008 | Becker |
| 2008/0215083 A1 | 9/2008 | Becker |
| 2008/0228085 A1 | 9/2008 | Jenkins et al. |
| 2008/0234720 A1 | 9/2008 | Chang et al. |
| 2008/0243140 A1 | 10/2008 | Gopferich |
| 2008/0262508 A1 | 10/2008 | Clifford et al. |
| 2008/0262509 A1 | 10/2008 | Clifford et al. |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0319424 A1 | 12/2008 | Muni et al. |
| 2009/0017090 A1 | 1/2009 | Arensdorf et al. |
| 2009/0028923 A1 | 1/2009 | Muni et al. |
| 2009/0030274 A1 | 1/2009 | Goldfarb et al. |
| 2009/0047326 A1 | 2/2009 | Eaton et al. |
| 2009/0088677 A1 | 4/2009 | Cohen |
| 2009/0088728 A1 | 4/2009 | Dollar et al. |
| 2009/0093823 A1 | 4/2009 | Chang et al. |

(56) References Cited

U.S. PATENT DOCUMENTS

| | | | |
|---|---|---|---|
| 2009/0156980 A1 | 6/2009 | Eaton et al. |
| 2009/0163890 A1 | 6/2009 | Clifford et al. |
| 2009/0187089 A1 | 7/2009 | Say et al. |
| 2009/0187098 A1 | 7/2009 | Makower et al. |
| 2009/0192492 A1 | 7/2009 | Eaton et al. |
| 2009/0198216 A1 | 8/2009 | Muni et al. |
| 2009/0227945 A1 | 9/2009 | Eaton et al. |
| 2009/0240112 A1 | 9/2009 | Goldfarb et al. |
| 2009/0240237 A1 | 9/2009 | Goldfarb et al. |
| 2009/0312745 A1 | 12/2009 | Goldfarb et al. |
| 2010/0087811 A1 | 4/2010 | Herrin et al. |
| 2010/0114066 A1 | 5/2010 | Makower et al. |
| 2010/0121308 A1 | 5/2010 | Muni et al. |
| 2010/0174308 A1 | 7/2010 | Chang et al. |
| 2010/0174366 A1 | 7/2010 | Avior |
| 2010/0198191 A1 | 8/2010 | Clifford et al. |
| 2010/0198302 A1 | 8/2010 | Shalev |
| 2010/0274188 A1 | 10/2010 | Chang et al. |
| 2010/0290244 A1 | 11/2010 | Nath |
| 2011/0166190 A1 | 7/2011 | Anderson et al. |

FOREIGN PATENT DOCUMENTS

| | | |
|---|---|---|
| CN | 2352818 | 12/1999 |
| DE | 03202878 | 8/1983 |
| DE | 4032096 | 4/1992 |
| DE | 04032096 | 4/1992 |
| DE | 04406077 | 9/1994 |
| DE | 08810044 | 11/1998 |
| DE | 29923582 | 12/2000 |
| DE | 10104663 | 8/2002 |
| DE | 10105592 | 8/2002 |
| EP | 0129634 | 1/1985 |
| EP | 0257605 | 3/1988 |
| EP | 0355996 | 2/1990 |
| EP | 0418391 | 3/1991 |
| EP | 0427852 | 5/1991 |
| EP | 0 585 757 | 3/1994 |
| EP | 0623582 | 11/1994 |
| EP | 0624349 | 11/1994 |
| EP | 0744400 | 11/1996 |
| EP | 0585757 | 6/1997 |
| EP | 0893426 | 1/1999 |
| EP | 1042998 | 10/2000 |
| EP | 1166710 | 1/2002 |
| EP | 1413258 | 4/2004 |
| EP | 1944053 | 7/2008 |
| FR | 2859377 | 3/2005 |
| FR | 2916144 | 11/2008 |
| GB | 2125874 | 3/1984 |
| GB | 2305174 | 4/1997 |
| JP | 53-067935 | 6/1978 |
| JP | 10-24098 | 1/1989 |
| JP | 3-503011 | 7/1991 |
| JP | 3-504935 | 10/1991 |
| JP | 4-221313 | 8/1992 |
| JP | 5-211985 | 8/1993 |
| JP | 6-277296 | 10/1994 |
| JP | 7-327916 | 12/1995 |
| JP | 8-317989 | 12/1996 |
| JP | 11-507251 | 6/1999 |
| JP | 2000-501634 | 2/2000 |
| JP | 2001-501846 | 2/2001 |
| JP | 2001-095815 | 4/2001 |
| JP | 2001-526077 | 12/2001 |
| JP | 2002-028166 | 1/2002 |
| JP | 2002-508214 | 3/2002 |
| JP | 2002-537908 | 11/2002 |
| JP | 2002-538850 | 11/2002 |
| JP | 2003-062080 | 3/2003 |
| JP | 2003-521327 | 7/2003 |
| JP | 2004-357728 | 12/2004 |
| JP | 2005-532869 | 11/2005 |
| RU | 2213530 | 10/2003 |
| SU | 1662571 | 7/1991 |
| WO | WO 90/11053 | 10/1990 |
| WO | WO 90/14865 | 12/1990 |
| WO | WO 91/17787 | 11/1991 |
| WO | WO 92/15286 | 9/1992 |
| WO | WO 9215286 A1 * | 9/1992 |
| WO | WO 92/22350 | 12/1992 |
| WO | WO 94/12095 | 6/1994 |
| WO | WO 96/29071 | 9/1996 |
| WO | WO 97/24161 | 6/1997 |
| WO | WO 99/24106 | 5/1999 |
| WO | WO 99/30655 | 6/1999 |
| WO | WO 99/32041 | 7/1999 |
| WO | WO 00/09192 | 2/2000 |
| WO | WO 00/23009 | 4/2000 |
| WO | WO 00/51672 | 9/2000 |
| WO | WO 00/53252 | 9/2000 |
| WO | WO 01/45572 | 6/2001 |
| WO | WO 01/54558 | 8/2001 |
| WO | WO 01/56481 | 8/2001 |
| WO | WO 01/70325 | 9/2001 |
| WO | WO 01/74266 | 10/2001 |
| WO | WO 01/97895 | 12/2001 |
| WO | WO 02/062269 | 8/2002 |
| WO | WO 03/049603 | 6/2003 |
| WO | WO 03/063703 | 8/2003 |
| WO | WO 03/105657 | 12/2003 |
| WO | WO 2004/006788 | 1/2004 |
| WO | WO 2004/018980 | 3/2004 |
| WO | WO 2004/026391 | 4/2004 |
| WO | WO 2004/082525 A2 | 9/2004 |
| WO | WO 2004/082525 A3 | 9/2004 |
| WO | WO 2005/018730 | 3/2005 |
| WO | WO 2005/077450 | 8/2005 |
| WO | WO 2005/089670 | 9/2005 |
| WO | WO 2005/117755 | 12/2005 |
| WO | WO 2006/034008 | 3/2006 |
| WO | WO 2006/078884 | 7/2006 |
| WO | WO 2006/107957 | 10/2006 |
| WO | WO 2006/116597 | 11/2006 |
| WO | WO 2006/118737 | 11/2006 |
| WO | WO 2006/135853 | 12/2006 |
| WO | WO 2007/111636 | 10/2007 |
| WO | WO 2007/124260 | 11/2007 |
| WO | WO 2008/036149 | 3/2008 |
| WO | WO 2008/045242 | 4/2008 |
| WO | WO 2008/051918 | 5/2008 |
| WO | WO 2008/134382 | 11/2008 |

OTHER PUBLICATIONS

Aust, R., et al 'The Functional Size of the Human Maxillary Ostium in Vivo' Acta. Otolaryn. (1978) vol. 78 pp. 432-435.

Baim, D.S., MD Grossman's Cardiac Catheterization, Angiography, and Intervention (2000) Lippincott Williams & Wilkins pp. 76, 84 & 214.

Barrett, S. 'Be Wary of Neurocranial Restructuring (NCR)' Chirobase (available at: http://www.chirobase.org/06DD/ncr.html) (Jul. 2003.).

Bartal, N. 'An Improved Stent for Use in the Surgical Management of Congenital Posterior Choanal Atresia' J. Laryngol. Otol. (1988) vol. 102 pp. 146-147.

Becker, A.E. 'Restenosis After Angioplasty' The Lancet (1988) vol. 331, No. 8584 p. 532.

Benninger et al. Adult Chronic Rhinosinusitis: Definitions, Diagnosis, Epidemiology, and Pathophysiology' Arch Otolarygol Head and Neck Surg. (Sep. 2003) vol. 129 pp. S1-S32.

Bent et al. 'The Frontal Cell as a Cause of Frontal Sinus Obstruction' American Journal of Rhinology. (1994) vol. 8, No. 4 pp. 185.

Binner et al. 'Fibre-Optic Transillumination of the Sinuses: A Comparison of the Value of Radiography and Transillumination in Antral Disease' Clinical Otolaryngology. (1978) vol. 3 pp. 1-11.

Brown, C.L. et al 'Safety and Feasibility of Balloon Catheter Dilation of Paranasal Sinus Ostia: A Preliminary Investigation' Annals of Otology, Rhinology & Laryngology (2006) vol. 115, No. 4 pp. 293-299.

(56) References Cited

OTHER PUBLICATIONS

Bumm, P., H. Kaiser et al 'Cortizontherapie, Corticoide in Klinik and Praxis' Thieme, Stuggart (1992) pp. 390-401 [Summary of textbook].

Casiano et al. 'Endoscopic Lothrop Procedure: the University of Miami Experience' American Journal of Rhinology (1998) vol. 12, No. 5 pp. 335-339.

Casserly, I.P. et al Chapter 7. 'Guides and Wires in Percutaneous Coronary Intervention' Strategic Approaches in Coronary Intervention (2006) Lippincott Williams & Wilkins pp. 91-99.

Chien, Y.W. et al. Nasal Systemic Drug Delivery, Drugs and the Pharmaceutical Sciences (1989) Marcel Dekker, Inc. Chapter 3, pp. 39-88.

Cohen et al 'Endoscopic Sinus Surgery: Where we are and where we're going' Current Opinion in Otolaryngology & Head and Neck Surgery (2005) vol. 13 pp. 32-38.

Colla, A. et al 'Trihaloacetylated Enol Ethers—General Synthetic Procedure and Heterocyclic Ring Closure Reactions with Hydroxylamine' Synthesis. (Jun. 1991) pp. 483-486.

Costa, M.N. et al 'Endoscopic Study of the Intranasal Ostium in External Dacryocystorhinostomy Postoperative. Influence of Saline Solution and 5-Flurorouracil' Clinics. (2007) vol. 62, Issue 1 pp. 41-46. http://www.scielo.br/scielo.php?pid=S1807-59322007000100007&script=sci_arttext.

Cussler, E.L. *Diffusion: Mass Transfer in Fluid Systems* Cambridge University Press (1996) [Summary of Txtbook].

Davis, G.E. et al., 'A Complication From Neurocranial Restructuring' Arch Otolaryngology Head Neck Surg. (Apr. 2003) vol. 129 pp. 472-474.

Deutschmann, R. et al. 'A Contribution to the Topical Treatment of [Maxillary] Sinusitis Preliminary Communication' Stomat DDR 26, (1976) pp. 585-592.

Domb, A. et al *Handbook of Biodegradable Polymers* Harwood Academic Publishers (1997) [Summary of textbook].

Draf, W. 'Endonasal Micro-Endoscopic Frontal Sinus Surgery: the Fulda Concept' Op Tech Otolaryngol Head Neck Surg. (1991) vol. 2 pp. 234-240.

Edmond et al 'ENT Surgical Stimulator' Nov. 1998 Final Report Cooperative Agreement No. DAMD17-95-2-5023.

Eremychev, V.A. 'Needles for Puncture and Drainage of the Maxillary Sinus' Meditsinskaya Tekhnika, No. 5 (1974) pp. 54-55.

Feldman, R.L. et al 'New Steerable, Ultra-Low-Profile, Fixed Wire Angioplasty Catheter: Initial Experience With the Cordis Orion™ Steerable PTCA Balloon Catheter' Cathet. Cardiovasc. Diagn. (1990) vol. 19, No. 2 pp. 142-145.

Ford, C.N. 'A Multipurpose Laryngeal Injector Device' Otolaryngol. Head Neck Surg. (1990) vol. 103, No. 1 pp. 135-137.

Friedman, M. M.D., et al 'Frontal Sinus Surgery: Endoscopic Technique' Operative Techniques in Otolaryngology—Head and Neck Surgery. (Jun. 2001) vol. 12, No. 2 pp. 60-65.

Friedman, et al 'Intraoperative and Postoperative Assessment of Frontal Sinus Patency by Transillumination' Laryngoscope. (Apr. 2000) vol. 110 pp. 683-684.

Friedman et al 'Middle Turbinate Medialization and Preservation in Endoscopic Surgery' Otolaryngol. Head Neck Surg. (2000) vol. 123, No. 1, Part 1. pp. 76-80.

Fung, M.K.T. 'How I Do It—Head and Neck and Plasic Surgery. A Targeted Problem and its Solution. Template for Frontal Osteoplastic Flap' Laryngoscope. (1986) vol. 96 pp. 578-579.

Gatot, A. et al., 'Early Treatment of Orbital Floor Fractures with Catheter Balloon in Children' Int. J. Pediatric Otorhinolaryngol (1991) vol. 21 pp. 97-101.

Gerus, I.I. et al 'β-Ethoxyvinyl Polyfluroroalkyl Ketones—Versatile Synthones in Fluoroorganic Chemistry' Journal of Fluorine Chemistry. (1994) vol. 69 pp. 195-198. Elsevier Science S.A.

Good, R.H. 'An Intranasal Method for Opening the Frontal Sinus Establishing the Largest Possible Drainage' Laryngoscope. (1908) vol. 18 pp. 266-274.

Gopferich 'Polymer Degradation and Erosion: Mechanisms and Applications' Eur. J. Pharm. Biophar. (1996) vol. 42 pp. 1-11.

Gorlov, D.V. et al 'Acylation of 2-Methoxypropene with Anhydrides and Halides of Perflurocarboxylic Acids in the Presence of Tertiary Amines' Russian Chemical Bulletin. (Sep. 1999) vol. 48 No. 9 pp. 1791-1792. Kluwer Academic/Plenum Publishers.

Gottman, et al. 'Balloon Dilatation in the Nasal Cavity and Paranasal Sinuses' CIRSE. (Sep. 25, 2004) pp. 1-27.

Gottman, et al. 'Balloon Dilatation of Recurrent Ostial Occlusion of the Front Sinus' Abstract No. B-04353. European Congress of Radiology. (Mar. 2, 2001).

Gottman, et al. 'Successful Treatment of Recurrent Post-Operative Frontal Sinus Stenoses by Balloon Dilatation' CIRSE. (Oct. 5, 2002).

Gupta, D. et al 'Dacryocystitis Secondary to an Iatrogenic Foreign Body in the Lacrimal Apparatus' Ear, Nose & Throat Journal (2009) http://findarticles.com/p/articles/mi_m0BUM/is_7_88/ai_n32428620/.

Hashim, et al 'Balloon Compression of the Intermaxillary Sinus for Intractable Post Traumatic Bleeding from the Maxillary Artery' Scandinavian Journal of Plastic and Reconstructive Surgery and Hand Surgery (1999) vol. 33 pp. 321-324.

Hojo, M. et al 'Electrophilic Substitutions of Olefinic Hydrogens II. Acylation of Vinyl Ethers and N Vinyl Amides' Chemistry Letters (1976) pp. 499-502.

Hopf, J.U.G. et al 'Miniature Endoscopes in Otorhinolaryngologic Applications' Min Invas Ther & Allied Technol. (1998) vol. 7, No. 3 pp. 209-218.

Hosemann, W. et al *A Dissection Course on Endoscopic Endonasal Sinus Surgery* (2005) Endo-Press, Tuttlingen pp. 4-37.

Hosemann, W. et al 'Endonasal Frontal Sinusotomy in Surgical Management of Chronic Sinusitis: A Critical Evaluation' American Journal of Rhinology (1997) vol. 11, No. 1 pp. 1-9.

Hosemann, M.E. et al 'Experimentelle Untersuchungen zur Wundheilung in den Nasennebenhohlen. II. Spontaner Wundschluss und medikamentose Effekte im standardisierten Wundmodell.' HNO 39 (1991) pp. 48-54.

Hosemann W.G. et al *Minimally Invasive Endonasal Sinus Surgery* Thieme, Stuttgart, New York (2000) [Summary of textbook].

Hosemann, M.E. et al 'Normal Wound Healing of the Paranasal Sinuses—Clinical and Experimental Investigations' Eur Arch Otorhinolaryngol. (1991) vol. 248 pp. 390-394.

Hosemann, W. et al 'Weiterbehandlung nach Nasennebenhohleneingriffen, Part 2: Theapeutische Maβnahmen' HNO akutell 7 (1999) pp. 291-302.

Hospital Corpsman Sickcall Screener's Handbook. Naval Hospital Great Lakes (Apr. 1999) http://www.brooksidepress.org/Products/Operationa.Medicine/DATA. 2001 pp. 1-6.

Hybels, R.L. 'Transillumination During Osteoplastic Frontal Sinusotomy' The Laryngoscope (Sep. 1981) vol. 91 pp. 1560.

Ijaduola, T.G.A. 'Use of a Foley Catheter for Short-Term Drainage in Frontal Sinus Surgery' The Journal of Laryngology and Otology. (1989) vol. 103 pp. 375-378.

Ingals, F. 'New Operation and Instruments for Draining the Frontal Sinus' Ann. Otol Rhinol Laryngol. (1905) vol. 14 pp. 515-519.

Iro, H. et al 'A New Device for Frontal Sinus Endoscopy: First Clinical Report' Otolaryngol. Head Neck Surg. (2001) vol. 125 No. 6 pp. 613-616.

Jacobs, J.B. '100 Years of Frontal Sinus Surgery' Laryngoscope. (1997) vol. 107 pp. 1-36.

Kennedy, D.W., M.D. et al *Diseases of the Sinuses Diagnosis and Management* (Copyright 2001) by B.C. Decker Inc.

Khomutov, S.M. et al 'Dissolution of a Mixture of Steroids in Cyclodextrin Solutions: a Model Description' Pharmaceutical Chemistry Journal. (Nov. 2001) vol. 35, No. 11 pp. 627-629.

Kingdom, T.T. et al 'Image-Guided Surgery of the Sinuses: Current Technology and Applications' Otolaryngol. Clin. North Am. (Apr. 2004) vol. 37, No. 2 pp. 381-400.

Klossek, J.M. et al 'Local Safety of Intranasal Triamcinolone Acetonide: Clinical and Histological Aspects of Nasal Mucosa in the Long-Term Treatment of Perennial Allergic Rhinitis' Rhinology (2001) vol. 39, No. 1 pp. 17-22.

Kozlov et al 'Diagnosis and Treatment of Sinusitis by Yamik Sinus Catheters' Rhinology (1996) vol. 34. pp. 123-124.

(56) References Cited

OTHER PUBLICATIONS

Kuhn, et al. 'The Agger Nasi Cell in Frontal Recess Obstruction: An Anatomic, Radiology and Clinical Correlation' Operative Techniques in Otolaryngology—Head and Neck Surgery (1991) vol. 2, No. 4 pp. 226-231.

Laliberte F. et al 'Clinical and Pathologic Methods to Assess the Long-Term Safety or Nasal Corticosteroids' Allergy (2000) vol. 55, No. 8 pp. 718-722.

Lang, E.V. et al 'Access Systems for Puncture at an Acute Angle' J. Vasc. Interv. Radiol. (1995) vol. 6, No. 5 pp. 711-713.

Lanza, D.C. 'Postoperative Care and Avoiding Frontal Recess Stenosis' International Advanced Sinus Symposium. General Session Abstracts. Jul. 21-24, 1993.

Large, G.C. 'Crystalline Tetracycline Hydrochloride in the Treatment of Acute and Chronic Maxillary Sinusitis' Canad. M. A. J. (1958) vol. 79 pp. 15-16.

Lund, V.J. 'Maximal Medical Therapy for Chronic Rhinosinusitis' Otolaryngol Clin N Am. (2005) vol. 38 pp. 1301-1310.

Maran, A.G.D. et al 'The Use of the Foley Catheter in the Tripod Fracture' J. Laryngol. Otol (1971) vol. 85, Issue 9 pp. 897-902.

May, M. et al 'Frontal Sinus Surgery: Endonasal Drainage Instead of an External Osteopolstic Approach' Op Tech Otolaryngo Head Neck Surgery (1995) vol. 6, No. 3 pp. 184-192.

Medtronic, xomed.com-MicroFrance Catalog Browser. http://www.xomcat.com/xomfrance/index.php?zone=both&cat=18&sub=58&prodline=1272 (Dec. 31, 2003) pp. 1-2.

Mehan, V.K. et al 'Coronary Angioplasty through 4 French Diagnostic Catheters' Cathet. Cardiovasc. Diagn. (1993) vol. 30, No. 1 pp. 22-26.

Mellor, J.M. et al 'Synthesis of Trifluromethylnaphthalenes' Tetrahedron (2000) vol. 56 pp. 10067-10074. Elseview Science Ltd.

Metson, R. et al 'Endoscopic Treatment of Sphenoid Sinusitis' Otolaryngol. Head Neck Surg. (1996) vol. 114, No. 6 pp. 736-744.

Metson, R. 'Holmium: YAG Laser Endoscopic Sinus Surgery: A Randomized Controlled Study' Laryngoscope (Jan. 1996) vol. 106, Issue 1, Supplement 77 pp. 1-18.

Miller et al. 'Management of Fractures of the Supraorbital Rim' Journal of Trauma (Jul. 1978) vol. 18, No. 7 pp. 507-512.

Min, Y-G et al. 'Mucociliary Activity and Histopathology of Sinus Mucosa in Experimental Maxilary Sinusitis: A Comparison of Systemic Administration of Antibiotic and Antibiotic Delivery by Polylactic Acid Polymer' Laryngoscope (Aug. 1995) vol. 105 pp. 835-842.

Mols, B. 'Moveable Tool Tip for Keyhole Surgery' Delft Outlook (2005) vol. 3 pp. 13-17.

Mooney, M.R. et al 'Monorail™ Piccolino Catheter: A New Rapid Exchange/Ultralow Profile Coronary Angioplasty System' Cathet. Cardiovasc. Diagn. (1990) vol. 20, No. 2 pp. 114-119.

Moriguchi, T. et al 'Addition-Elimination Reaction in the Trifluoroacetylation of Electron-Rich Olefins' J. Org. Chem. (1995) vol. 60, No. 11 pp. 3523-3528. American Chemical Society.

Park, K. et al *Biodegreadable Hydrogels for Medicinal Substance Delivery* (1993) Technomic Publishing Inc. Lancaster.

Piccirillo, J.F. et al 'Psychometric and Clinimetric Validity of the 20-Item Sino-Nasal Outcome Test (SNOT-20)' Otolaryngol. Head Neck Surg (2002) vol. 126, No. 1 pp. 41-47.

Piers, et al 'A Flexible Distal Tip with Two Degrees of Freedom for Enhanced Dexterity in Endoscopic Robot Surgery' Proceedings 13th Micromechanics Europe Workshop (2002) pp. 271-274.

Podoshin, L. et al 'Balloon Technique for Treatment of Frontal Sinus Fractures' The Journal of Laryngology & Otology (1967), vol. 81. pp. 1157-1161.

Pownell, P.H. et al 'Diagnostic Nasal Endoscopy' Plastic & Reconstructive Surgery (1997) vol. 99, Iss. 5 pp. 1451-1458.

Prince et al 'Analysis of the Intranasal Distribution of Ointment' J Otolaryngol. (1997) vol. 26 pp. 357-360.

Ramsdale, D.R. *Illustrated Coronary Intervention A case-oriented approach* (2001) Martin Dunitz Ltd. pp. 1-5.

Ritter, F.N. et al *Atlas of Paranasal Sinus Surgery* (1991) Igaku-Shoin Medical Pub. pp. 1-81.

Robison, J. Mathews, M.D. 'Pressure Treatment of Maxillary Sinusitis' J.A.M.A. (May 31, 1952) pp. 436-440.

Robison, J. Mathews, M.D. 'Pressure Treatment of Purulent Maxillary Sinusitis' Texas State Journal of Medicine. (May 1951) pp. 281-288.

Sama, A. et al 'Current Opinions on the Surgical Management of Frontal Sinus Disease' ENT News. www.pinpointmendical.com/ent-news (2009) vol. 17 No. 6 pp. 60-63.

Sanborn, T.A., et al 'Percutaneous Endocardial Transfer and Expression of Genes to the Myocardium Utilizing Fluropscopic Guidance' Catheter Cardiovasc. Interv. (2001) vol. 52, No. 2 pp. 260-266.

*Sawbones Catalog* 2001, Pacific Research Laboratories, Inc., Vashon, Washington 98070 USA.

Saxon, R.R., et al 'Technical Aspects of Accessing the Portal Vein During the TIPS Procedure' J. Vasc. Interv. Radiol. (1997) vol. 8, No. 5 pp. 733-744.

Schaefer, S.D., M.D. *Rhinology and Sinus Disease A Problem-Oriented Approach* (Copyright 1988) by Mosby, Inc.

Shah, N.J. et al 'Endoscopic Pituitary Surgery—A Beginner's Guide' Indian Journal of Otolaryngology and Head and Neck Surgery (2004) vol. 56, No. 1 pp. 71-78.

Shah, N.J. 'Functional Endoscopic Sinus Surgery' (1999); found at www.bhj.org/journal/1999_4104_oct99/sp_659.htm.

Single-Pole and Multi-Pole Lightguides for UV Spot Light Curing Systems. http://www.dymax.com/products/curing_equipment/lightguids/light. (2004) pp. 1-2.

Sobol, et al 'Sinusitis, Maxillary, Acute Surgical Treatment.' eMedicine. Retrieved from the Internet: <<http://emedicine.medscape.com/article/862030-print>> (Nov. 16, 2010) pp. 1-11.

St. Croix, et al 'Genes Expressed in Human Tumor Endothelium' Science (May 15, 2000) vol. 289 pp. 1197-1202.

Stammberger H. 'Komplikationen entzundlicher Nasennebenhohlenerkrankungen eischließlich iatrogen bedingter Komplikationen.' Eur Arch Oti-Rhino-Laryngol Suppl. (Jan. 1993) pp. 61-102.

Stammberger, et al 'Special Endoscopic Anatomy of the Lateral Nasal Wall and Ethmoidal Sinuses' Functional Endoscopic Sinus Surgery. (1991) Ch. 3, pp. 49-87.

Strohm et al Die Behandlung von Stenosen der oberen Luftwege mittels rontgenologisch gesteuerter Ballondilation (Sep. 25, 1999).

Strohm, et al 'Le Traitement Des Stenoses Voies Aeriennes Superieures Par Dilation Au Balloon' Sep. 25, 1999.

Strohm, et al 'Treatment of the Stenoses of the Upper Air Routes by Balloon Dilation' Sudwestdeutscher (Sep. 25, 1999) Abstract 45 pp. 1-3.

SurgTrainer Product Information 'Incisive Human Nasal Model for ESS Training' Surg Trainer, Ltd. Ibaraki, Japan (2204) http://www1.accsnet.ne.jp/~juliy/st/en/partslist.html.

Tabor, M.H. et al 'Symptomatic Bilateral Nasolacrimal Duct Cysts in a Newborn-Rhinoscopic Clinic' Ear, Nost & Throat Journal (2003) http://findarticles.com/p/articles/mi_m0BUM/is_2_82/ai_98248244 pp. 1-3.

Tarasov, D.I. et al. 'Application of Drugs Based on Polymers in the Treatment of Acute and Chronic Maxillary Sinusitis' Vestn Otorinolaringol. (1978) vol. 6 pp. 45-47.

Terumo. Medi-Tech. Boston Scientific. (1993) Ad for Glidewire.

The Operating Theatre Journal (www.otjonline.com) 'Disposable Medical Device for Wound Disclosure/The Tristel Purple Promotion—A Collaboration between Tristel plc and Karl Storz Endoscopy (UK) Ltd.' pp. 4 [retrieved on Nov. 30, 2010]. Retrieved from the Internet.

Weber, R. et al 'Endonasale Stirnhohlenchirugie mit Langzeiteinlage eines Platzhalters' Laryngol. Rhinol. Otol. (1997) vol. 76 pp. 728-734. (English Abstract).

Weber, R. et al 'Videoendscopic Analysis of Nasal Steroid Distribution' Rhinology (1999) vol. 37 pp. 69-73.

Weiner, R.I., D.O. et al 'Development and Application of Transseptal Left Heart Catheterization' Cathet. Cardiovasc. Diagn. (1988) vol. 15, No. 2 pp. 112-120.

Wiatrak, B.J. et al 'Unilateral Choanal Atresia: Initial Presentation and Endoscopic Repair' International Journal of Pediatric Otorhinolaryngology (1998) vol. 46 pp. 27-35.

(56) References Cited

OTHER PUBLICATIONS

Woog, et al. 'Paranasal Sinus Endoscopy and Orbital Fracture Repair' Arch Ophthalmol. (May 1998) vol. 116 pp. 688-691.
Wormald, P.J. et al 'The 'Swing-Door' Technique for Uncinectomy in Endoscopic Sinus Surgery' The Journal of Laryngology and Otology (1998) vol. 112 pp. 547-551.
Yamauchi, Y. et al 'Development of a Silicone Model for Endoscopic Sinus Surgery' proc International Journal of Computer Assisted Radiology and Surgery (1999) vol. 99 pp. 1039.
Yamauchi, Y. et al 'A Training System for Endoscopic Sinus Surgery with Skill Evaluation' Computer Assisted Radiology and Surgery (2001) with accompanying poster presentation.
Yanagisawa et al 'Anterior and Posterior Fontanelles.' Ear, Nose & Throat Journal (2001) vol. 80. p. 10-12.
Zimarino, M., MD et al 'Initial Experience with the Europass™: A New Ultra-Low Profile Monorail Balloon Catheter' Cathet. Cardiovasc. Diagn. (1994) vol. 33, No. 1 pp. 76-79.
http://www.invotec.net/rhinology/ksplint.html. K-Splint Internal Nasal Splints; Jan. 25, 2007.
http://www.doylemedical.com/nasalsplints.htm; Doyle Nasal Splints; Jan. 25, 2007.
http://www.technologyforlife.com.au/ent/nasal.html; Nasal Surgery and Accessories; Jan. 25, 2007.
EP Communication dated Sep. 4, 2008 re: EP 05773189.
EP Communication dated Jun. 19, 2009 re: EP 05773189.
Examination Report dated Feb. 22, 2006 re: 02716734.5.
Examination Report dated Feb. 8, 2007 re: 02716734.5.
Examiners First Report dated Apr. 8, 2010 re: AU2005274794.
European Search Report and Search Opinion dated Sep. 11, 2009 from EP06815174.
European Search Report dated Sep. 27, 2011 re: EP10182961.
European Search Report dated Sep. 29, 2011 re: EP10182893.
International Preliminary Report on Patentability dated Aug. 25, 2006 from PCT/US05/25371.
International Preliminary Report on Patentability dated Oct. 4, 2007 from PCT/US06/002004.
International Preliminary Report on Patentability dated Nov. 27, 2008 from PCT/US07/11449.
International Preliminary Report on Patentability dated Apr. 16, 2009 from PCT/US07/021170.
International Preliminary Report on Patentability dated May 14, 2009 from PCT/US06/36960.
International Preliminary Report on Patentability dated Oct. 22, 2009 from PCT/US08/059786.
International Preliminary Report on Patentability dated Nov. 5, 2009 from PCT/US08/061343.
International Search Report dated May 23, 2002 from PCT/EP02/01228.
International Search Report dated Jun. 3, 2002 from PCT/EP02/01228.
International Search Report and Written Opinion dated Apr. 10, 2006 from PCT/US05/25371.
International Search Report dated May 8, 2007 from PCT/US2006/16026.
International Search Report and Written Opinion dated Aug. 17, 2007 from PCT/US05/13617.
International Search Report and Written Opinion dated Aug. 29, 2007 from PCT/US06/002004.
International Search Report dated Sep. 25, 2007 from PCT/US06/37167.
International Search Report dated Oct. 19, 2007 from PCT/US07/03394.
International Search Report and Written Opinion dated May 29, 2008 from PCT/US07/021170.
International Search Report dated May 29, 2008 from PCT/US07/21922.
International Search Report and Written Opinion dated Jul. 1, 2008 from PCT/US06/22745.
International Search Report dated Jul. 3, 2008 from PCT/US2006/029695.
International Search Report dated Jul. 7, 2008 from PCT/US07/16213.
International Search Report dated Jul. 8, 2008 from PCT/US07/11474.
International Search Report and Written Opinion dated Jul. 17, 2008 from PCT/US06/36960.
International Search Report and Written Opinion dated Jul. 21, 2008 from PCT/US05/33090.
International Search Report dated Aug. 25, 2008 from PCT/US2008/000911.
International Search Report dated Sep. 10, 2008 dated PCT/US07/16212.
International Search Report and Written Opinion dated Sep. 12, 2008 from PCT/US07/16214.
International Search Report and Written Opinion dated Sep. 17, 2008 from PCT/US08/059786.
International Search Report and Written Opinion dated Sep. 17, 2008 from PCT/US08/061343.
International Search Report and Written Opinion dated Oct. 1, 2008 from PCT/US07/11449.
International Search Report dated Oct. 15, 2008 from PCT/US2008/061048.
International Search Report dated Nov. 30, 2009 re: PCT/US2009/057203.
International Search Report from PCT Application No. PCT/US2009/057203 dated Nov. 30, 2009 as issued by the European Patent Office as searching authority.
International Search Report dated Dec. 10, 2009 re: PCT/US2009/052236.
International Search Report dated Dec. 16, 2009 re: PCT/US2009/050800.
International Search Report dated Mar. 31, 2010 re: PCT/US2009/069143.
International Search Report dated Jul. 8, 2010 re: PCT/US2010/027837.
International Search Report dated Oct. 6, 2010 re: PCT/US2010/040548.
International Search Report dated Mar. 25, 2011 re: PCT/US2010/062161.
International Search Report dated Mar. 28, 2011 re: PCT/US2010/061850.
International Search Report dated Mar. 31, 2011 re: PCT/US2010/060898.
International Search Report dated Aug. 9, 2011 re: PCT/US2011/038751.
International Search Report dated May 18, 2012 re: PCT/US2011/052321.
Partial European Search Report dated Sep. 20, 2007 re: 07252018.
Partial European Search Report dated Mar. 25, 2008 re: 07252018.
Partial International Search Report dated Feb. 7, 2012 re: PCT/US2011/052321.
Supplemental European Search Report dated Jun. 2, 2008 re: EP05773189.
Supplemental European Search Report dated Jul. 1, 2009 re: EP06815285.
Supplemental European Search Report dated Jan. 29, 2010 from EP07836108.
Supplemental European Search Report dated Feb. 2, 2010 re: EP07836109.
Supplemental European Search Report dated Feb. 17, 2010 re: EP07836110.
Supplemental European Search Report dated Mar. 1, 2010 re: EP05778834.
Supplemental European Search Report dated Mar. 16, 2010 from EP06718986.
Supplemental European Search Report dated Jun. 22, 2010 re: EP06784759.
Supplemental European Search Report dated Sep. 23, 2010 re: EP08746715.
Supplemental Partial European Search Report dated Nov. 19, 2010 re: EP06751637.
Supplemental European Search Report dated Jan. 28, 2011 re: 07777004.

(56) References Cited

OTHER PUBLICATIONS

Supplemental European Search Report dated Mar. 31, 2011 re: EP05798331.
Supplemental European Search Report dated Aug. 30, 2011 re: EP06800540.
Supplemental European Search Report dated Sep. 29, 2011 re: EP07750248.
U.S. Appl. No. 10/259,300, filed Sep. 30, 2002.
U.S. Appl. No. 10/259,630, filed Sep. 30, 2002.
U.S. Appl. No. 10/470,881, filed Feb. 4, 2004.
U.S. Appl. No. 10/829,917, filed Apr. 21, 2004.
U.S. Appl. No. 10/912,578, filed Aug. 4, 2004.
U.S. Appl. No. 10/944,270, filed Sep. 17, 2004.
U.S. Appl. No. 11/037,548, filed Jan. 18, 2005.
U.S. Appl. No. 11/116,118, filed Apr. 26, 2005.
U.S. Appl. No. 11/150,847, filed Jun. 10, 2005.
U.S. Appl. No. 11/193,020, filed Jul. 29, 2005.
U.S. Appl. No. 11/234,395, filed Sep. 23, 2005.
U.S. Appl. No. 11/347,147, filed Feb. 2, 2006.
U.S. Appl. No. 11/355,512, filed Feb. 16, 2006.
U.S. Appl. No. 11/436,892, filed May 17, 2006.
U.S. Appl. No. 11/436,897, filed May 17, 2006.
U.S. Appl. No. 11/438,090, filed May 18, 2006.
U.S. Appl. No. 11/522,497, filed Sep. 15, 2006.
U.S. Appl. No. 11/527,773, filed Sep. 25, 2006.
U.S. Appl. No. 11/544,009, filed Oct. 4, 2006.
U.S. Appl. No. 11/647,530, filed Dec. 27, 2006.
U.S. Appl. No. 11/648,159, filed Dec. 29, 2006.
U.S. Appl. No. 11/655,794, filed Jan. 18, 2007.
U.S. Appl. No. 11/725,151, filed Mar. 15, 2007.
U.S. Appl. No. 11/789,704, filed Apr. 24, 2007.
U.S. Appl. No. 11/789,705, filed Apr. 24, 2007.
U.S. Appl. No. 11/803,695, filed May 14, 2007.
U.S. Appl. No. 11/925,540, filed Oct. 26, 2007.
U.S. Appl. No. 11/926,326, filed Oct. 29, 2007.
U.S. Appl. No. 11/926,565, filed Oct. 29, 2007.
U.S. Appl. No. 11/928,097, filed Oct. 30, 2007.
U.S. Appl. No. 12/011,100, filed Jan. 23, 2008.
U.S. Appl. No. 12/100,361, filed Apr. 9, 2008.
U.S. Appl. No. 12/117,582, filed May 8, 2008.
U.S. Appl. No. 12/117,672, filed May 8, 2008.
U.S. Appl. No. 12/117,961, filed May 9, 2008.
U.S. Appl. No. 12/118,931, filed May 12, 2008.
U.S. Appl. No. 12/120,902, filed May 15, 2008.
U.S. Appl. No. 12/122,884, filed May 19, 2008.
U.S. Appl. No. 12/340,226, filed Dec. 19, 2008.
U.S. Appl. No. 12/341,602, filed Dec. 22, 2008.
U.S. Appl. No. 12/502,101, filed Jul. 13, 2009.
U.S. Appl. No. 60/844,874, filed Sep. 15, 2006.
U.S. Appl. No. 60/922,730, filed Apr. 9, 2007.
U.S. Appl. No. 61/052,413, filed May 12, 2008.
U.S. Appl. No. 61/084,949, filed Jul. 30, 2008.
USPTO Office Action dated Sep. 16, 2005 in U.S. Appl. No. 10/259,300.
USPTO Office Action dated Jul. 7, 2006 in U.S. Appl. No. 10/259,300.
USPTO Office Action dated Feb. 13, 2007 in U.S. Appl. No. 10/259,300.
USPTO Office Action dated May 29, 2007 in U.S. Appl. No. 10/912,578.
USPTO Office Action dated Oct. 9, 2007 in U.S. Appl. No. 10/259,300.
USPTO Office Action dated Oct. 18, 2007 in U.S. Appl. No. 11/037,548.
USPTO Office Action dated Nov. 14, 2007 in U.S. Appl. No. 10/912,578.
USPTO Office Action dated Nov. 28, 2007 in U.S. Appl. No. 11/234,395.
USPTO Office Action dated Dec. 6, 2007 in U.S. Appl. No. 11/037,548.
USPTO Office Action dated Dec. 10, 2007 in U.S. Appl. No. 10/912,578.
USPTO Office Action dated Jan. 24, 2008 in U.S. Appl. No. 10/259,300.
USPTO Office Action dated Apr. 9, 2008 in U.S. Appl. No. 11/037,548.
USPTO Office Action dated Sep. 12, 2008 in U.S. Appl. No. 10/829,917.
USPTO Office Action dated Oct. 6, 2008 in U.S. Appl. No. 10/259,300.
USPTO Office Action dated Oct. 29, 2008 in U.S. Appl. No. 11/347,147.
USPTO Office Action dated Nov. 7, 2008 in U.S. Appl. No. 10/944,270.
USPTO Office Action dated Nov. 17, 2008 in U.S. Appl. No. 10/829,917.
USPTO Office Action dated Nov. 17, 2008 in U.S. Appl. No. 12/117,582.
USPTO Office Action dated Nov. 17, 2008 in U.S. Appl. No. 12/118,931.
USPTO Office Action dated Nov. 25, 2008 in U.S. Appl. No. 12/117,961, filed May 9, 2008.
USPTO Office Action dated Dec. 5, 2008 in U.S. Appl. No. 12/120,902, filed May 15, 2008.
USPTO Office Action dated Jan. 28, 2009 in U.S. Appl. No. 10/944,270.
USPTO Office Action dated Feb. 4, 2009 in U.S. Appl. No. 11/347,147.
USPTO Office Action dated Mar. 3, 2009 in U.S. Appl. No. 12/117,582.
USPTO Office Action dated Mar. 4, 2009 in U.S. Appl. No. 12/118,931.
USPTO Office Action dated Mar. 17, 2009 in U.S. Appl. No. 11/690,127.
USPTO Office Action dated Mar. 18, 2009 in U.S. Appl. No. 10/829,917.
USPTO Office Action dated Mar. 23, 2009 in U.S. Appl. No. 11/804,309.
USPTO Office Action dated Mar. 23, 2009 in U.S. Appl. No. 11/926,326.
USPTO Office Action dated Apr. 21, 2009 in U.S. Appl. No. 10/944,270.
USPTO Office Action dated Jul. 30, 2009 in U.S. Appl. No. 12/118,931.
USPTO Office Action dated Aug. 6, 2009 in U.S. Appl. No. 11/347,147.
USPTO Office Action dated Aug. 6, 2009 in U.S. Appl. No. 12/117,582.
USPTO Office Action dated Aug. 6, 2009 in U.S. Appl. No. 12/117,961.
USPTO Office Action dated Aug. 28, 2009 in U.S. Appl. No. 11/150,847.
USPTO Office Action dated Oct. 21, 2009 in U.S. Appl. No. 12/120,902.
USPTO Office Action dated Nov. 9, 2009 in U.S. Appl. No. 10/829,917.
Shikani A. "A New Middle Meatal Antrostomy Stent for Functional Endoscopic Sinus Surgery". May 1994. Larynoscope 104: May 1994. pp. 638-641.
US Office Action Final dated Aug. 29, 2013 for U.S. Appl. No. 12/138,364.

* cited by examiner

SPACING DEVICE FOR RELEASING ACTIVE SUBSTANCES IN THE PARANASAL SINUS

BACKGROUND

1. Technical Field

The present invention relates to a spacing device (stent) for use in fenestrations of the paranasal sinus.

2. Related Art

About 5% of our population suffer from a chronic mucous membrane inflammation of the paranasal sinuses. In the course of an inflammation of this type, nasal polyps occur in every fifth patient. If corresponding symptoms occur and an attempt at medicinal treatment remains unsuccessful, the chronic sinusitis is approached surgically.

The paranasal sinus system consists of a series of cavities lined with mucous membrane and filled with air. The interruption of the natural secretion drainage from the remote paranasal sinus portions and the removal of natural ventilation are important in the occurrence of chronic sinusitis. The remote, diseased paranasal sinus portions are accordingly reventilated during cleaning-up interventions through newly created or extended accesses ("windows"). After healing, the natural secretion drainage of these reventilated compartments reappears.

Surgical treatment of chronic sinusitis has been transformed after the introduction of modern optical aids (rigid endoscopes, microscope). Nowadays, the "minimally invasive" clearing exclusively of those mucous membrane parts which have undergone an obviously irreversible change owing to the inflammation process predominates. Other reversibly changed or unaffected mucous membrane areas are spared as far as possible (Hosemann W G, Weber R K, Keerl R E, Lund V J: Minimally invasive endonasal sinus surgery. Thieme, Stuttgart, New York 2000).

If the frontal sinus mucous membrane is involved in the inflammatory modification of the sinus a surgical fenestration takes place towards the nose. This is carried out with special instruments (bent sharp spoons, special stamps, drills). Accesses of about 5 to a maximum of 10 mm in diameter are produced by routine "fenestration" of the frontal sinus. During healing of the wound these accesses narrow by about 1.5 mm.

If certain health factors are present, such as, for example intolerance of analgesics, a disproportionate tendency to scarred narrowing has to be taken into account (Hosemann W, Th. Kühnel, P. Held, W. Wagner, A. Felderhoff: Endonasal frontal sinusotomy in surgical management of chronic sinusitis—a critical evaluation. Am. J. Rhinology 11: 1-9 (1997)). In such cases it is advised to maximise the surgical access as a precaution. This "widened frontal sinus surgery" is subdivided into specific types (Draf W: Endonasal micro-endoscopic frontal sinus surgery: the Fulda concept. Op Tech Otolaryngol Head Neck Surg 2: 234-240 (1991); May M, Schaitkin B: Frontal sinus surgery: endonasal drainage instead of an external osteopolstic approach. Op Tech Otolaryngo Head Neck Surg 6: 184-192 (1995)).

As stated, the neo-ostium to the front sinus narrows to a greater or lesser extent, according to experience. To prevent this scarred stenosis it was already proposed at the start of the last century, i.e. long before the introduction of minimally invasive endoscopic surgery to insert a spacing device (stent). These spacing devices usually had the form of a small tube and were made of various materials: at the beginning rolled metal or metal braided in wires was used (Fletscher Ingals E: New operation and instruments for draining the frontal sinus. Ann Otol Rhinol Laryngol 14: 515-519 (1905), Good R H: An intranasal method for opening the frontal sinus establishing the largest possible drainage. Laryngoscope 18: 266-274 (1908)). In the last two decades silicone tubes were preferred (Stammberger H: Komplikationen entzündlicher Nasennebenhöhlenerkrankungen eischließlich iatrogen bedingter Komplikationen. Eur Arch Oto-Rhino-Laryngol Suppl 1993/1: 61-186).

Experience with spacing devices for stabilising the newly created frontal sinus access was not always, however, encouraging, apart from individual reports (Jacobs J B: 100 years of frontal sinus surgery. Laryngoscope 107: 1-36 (1997); Weber, R, W. Hosemann, W. Draf, R. Keerl, B. Schick, S. Schinzel: Denonasale Stirnhöhlenchirugie mit Langzeiteinlage eines Platzhalters. Laryngol. Rhinol. Otol. 76: 728-734 (1997).

Initially it remained unclear as to how long a spacing device of this type was required in the area of the operation. From animal experiments on wound healing, it became clear that a scarred narrowing of the frontal sinus access for a post-operative period of at least three months has to be assumed (Hosemann, M. E. Wigand, U. Göde, F. Länger, I. Dunker: Normal wound healing of the paranasal sinuses—clinical and experimental investigations, Eur. Arch, Otorhinolarylgol. 248: 390-394 (1991)). Accordingly, the spacing device would have to be used over eight to twelve weeks. Even with the correct duration in position a spacing device will often only delay and possibly reduce in scope the undesired scarred narrowing, without being able to prevent it completely. An additional medicinal treatment to reduce excessive wound reactions would have to take place here.

According to the present level of knowledge about wound healing processes in the nose the administration of medicinal substances such as, for example, corticosteroids, seems to be in a position to counteract, with a certain reliability, this tendency to regenerating mucous membrane for scarred stricture of the front sinus nose passage (Hosemann, M. E. Wigand, U. Göde, F. Länger, I. Dunker: Normal wound healing of the paranasal sinuses—clinical and experimental investigations. Eur. Arch. Otorhinolaryngol. 248: 390-394 (1991); Hosemann W, Göde U, Länger F, Wigan M E: Experimentelle Untersuchungen zur Wundheilung in den Nasennebenhöhlen. II. Spontaner Wundschluss und medikamentöse Effekte im standardisierten Wundmodell. HNO 3948-54 (1991); Hosemann W, Kühnel Th, Allert M H: Weiterbehandlung nach Nasennebenhöhleneingriffen, part 2: Theapeutische Maßnahmen, HNO aktuell 7: 291-302 (1999).

Unfortunately, conventional medicine forms such as salves or sprays do not reach into the problem region of the transition of frontal sinus and nose during routine application (Prince M E P, Lemckert R J: Analysis of the intranasal distribution of ointment. J Otolaryngol 26: 357-360 (1997); Weber R, Keerl R, Radziwill R, Schick B, Haspersen D, Dshambazov K, Mlynski G, Draf W: Videoendoscopic analysis of nasal steroid distribution. Rhinology 37: 69-73 (1999)).

Postoperative systemic administration of corticosteroids is certainly usual in rhinosurgery (Bumm P: Hals-Nasen-Ohrenkrankheiten. In: Kaiser H, Kley H K (Hrsg.) Cortizontherapie, Corticoide in Klinik und Praxis. Thieme, Stuttgart 1992, pages 390-401), but the treatment plans do not usually extend over the required duration of 8 weeks. Moreover, with longer-term systemic corticosteroid administration side effects of the treatment have to be increasingly taken into account.

The presently described problems show the need for systems which can in a controlled manner dispense the active substances such as, for example, corticosteroids over a longer period directly to the operation site.

A series of systems have been proposed for the controlled release of medicinal substances such as, for example implants of polymers loaded with a medicinal substance. U.S. Pat. No. 5,633,000 thus describes implants for the release of pain killers. The polymers used there release the active substance via diffusion. U.S. Pat. No. 5,019,372 describes that this release can be modulated by incorporation of magnetic particles and by application of alternating magnetic fields. If this formed body is designed with a correspondingly defined geometry the release of the active substances can be optimised such that they are released over the application period at a constant speed (U.S. Pat. No. 4,803,076).

The polymers used for such applications include, apart from biodegradable materials, non-biodegradable materials, i.e. those which do not decompose on contact with body fluids. Examples of such polymers are silicone, polyacrylate and ethylene vinyl acetate copolymer (U.S. Pat. No. 4,069,307). The last polymer group, in particular, was used for a series of systems for controlled release of active substances.

U.S. Pat. No. 3,393,073 thus describes a so-called reservoir system consisting of a medicinal substance reservoir which is surrounded by a polymer sheath regulating the release rate of the medicinal substance. Such systems were successfully used for the development of "intra-uterine devices" which release the active substance in the uterus (U.S. Pat. No. 3,967,618 and U.S. Pat. No. 4,016,251) and for producing therapeutic systems which release medicinal substances to the eye (U.S. Pat. No. 4,052,505).

Such systems were also described, as carrier systems with a microporous membrane controlling the discharge of the active substance, for introduction into various body cavities, such as for example, the ear, nose or the rectum (U.S. Pat. No. 3,948,254).

Those made of plastics are described in the area of "stents" for the treatment of paranasal sinuses, such as, for example in U.S. Pat. No. 5,693,065 or U.S. Pat. No. 5,336,163. U.S. Pat. No. 5,693,065 describes a stent for the nose area made of silicone rubber having a cylindrical shaft of which the leading end to be inserted into the nose is designed in the shape of the point of a spear, the base of the point connected to the shaft having a wider diameter than the shaft. The point is closed at the front and laterally has ribs with slits therebetween, the ribs expanding in the inserted state and thus ensuring the hold of the stent in the nose area.

An external diameter of 0.157 inches and an internal diameter of 0.118 inches is given as the dimensions for the shaft. The firm seat of the stent in the nose passage is only ensured, however, by the spreading of the spear-shaped point.

U.S. Pat. No. 5,336,163 relates to a stent for the nose area formed from a porous material and having a non-adhering, but slightly porous outer surface. The stent is formed from a material here which expands on contact with liquid.

U.S. Pat. No. 5,601,594 describes a stent for insertion into a nose aperture, the stent having a bent shape and being formed from a compressible material.

However, these are systems which are free of medicinal substances and the action of which only aims to keep open the accesses to the frontal sinus by physical/mechanical effects.

Despite this progress in the area of controlled release of active substances there has previously not been any indications that this technology could be usable for the post-operative care of sinus systems after minimally invasive clearing. Although so-called "stents" which prevent a tissue reconstruction are known these are described exclusively for the treatment of blood vessels and are accordingly geared to other biological needs.

U.S. Pat. No. 5,980,551 describes a stent for blood vessels, the stent having an inner support structure which may be formed from a wire and the support structure is surrounded by a biodegradable resorbable substrate. Biologically active microparticles which release active substances in a controlled manner can be embedded into this substrate.

Stents for suppressing the restenosis of coronary arteries have design features which clearly differ from the subject of the invention and therefore also make them unsuitable for application in the frontal sinus.

In many cases the "coronary stents" also require application aids. Such application aids are described in combination with a stent in U.S. Pat. No. 6,080,190 and U.S. Pat. No. 5,843,089. A serious problem of coronary stents to release active substances is the construction of the medicinal substance release system. Coronary stents generally consist of a stent body such as, for example, a wire braiding covered with medicinal substance-carrying polymers or sheathed in thin polymer films (U.S. Pat. No. 5,824,048, U.S. Pat. No. 5,700,286, U.S. Pat. No. 5,837,313, U.S. Pat. No. 5,679,400). The mechanical stability of these stents is geared to the needs of arteries and makes them unsuitable for application in the nasal sinus, as they are not mechanically stable enough.

Coronary stents are rotationally symmetrical hollow bodies and preferably have the geometry of a hollow cylinder. They can therefore not be fixed via thickenings at the cylinder end in a fenestration of the paranasal sinus. Moreover, a fenestration of the paranasal sinus is generally not uniformly round, but more or less irregular which creates additional problems with respect to anchoring. In general, coronary stents cannot have large wall thicknesses so as not to impede the blood flow.

Moreover, coronary stents differ from spacing devices for paranasal sinuses due to their function. The coronary stent is intended to expand the vessel in many cases. The front sinus spacing device, on the other hand, is inserted in a surgically applied passage which has bony (stable) walls. This passage was surgically newly formed; the coronary artery, on the other hand is left as a tube, but expanded.

A coronary stent is a permanent implant, it is completely absorbed by the body. The frontal sinus spacing device, on the other hand, is removed after a period of about 8 weeks.

The coronary stent is completely absorbed by the body. Blood flows in the interior of the coronary stent; the wall is completely colonised in the most favourable case by the body's own cells (endothelial cells). With the frontal sinus spacing device, complete absorption into the body is not desirable. Secretion from the mucous membrane surface should drain in the interior of the frontal sinus spacing device and ventilation should simultaneously be ensured. Colonisation of the interior of the spacing device with the body's own cells is neither anticipated nor desired.

On the other hand, the mucous membrane should widen at the outside of the frontal sinus spacing device. In this manner, once the spacing device has been removed, a passage lined with intact mucous membrane should remain.

A problem in the coronary stent is the formation of a clot with the risk of an occlusion which has to be suppressed by the administration of special medication. The frontal sinus spacing device does not require the administration of special medication.

It has been proposed to produce medical devices used in the body from a material loaded with active substance or to coat them therewith.

WO 96/29071 describes medical devices such as catheters or stents, on the surface of which antibacterial means are applied, the antibacterial means adhering to the surface owing to adhesive forces, without further aids being required.

It is proposed in general in WO 92/15286 to form medical devices from a polymer loaded with medicinal substance or to provide them with a coating thereof, stents also being mentioned for use in the nasal area, without more detail about the configuration of a stent of this type.

SUMMARY

It is the object of the invention to provide a spacing device suitable, in particular, for use in the paranasal sinus having not only adequate stability and a firm hold but simultaneously able to release in situ a desired active substance in a controlled manner, a controlled release of the required amount of active substance with the desired time course also being ensured over an adequately long period for the treatment.

In addition, the spacing device according to the invention allows an adequately large quantity of active substance to be received and stored, without impairment of the controlled release owing to interactions of the active substance contents.

According to the invention, this object is achieved by a spacing device as described herein.

In keeping with the above-mentioned requirements the ratio q of the external diameter $r_a$ to the internal diameter $r_i$ of the stent body is a value of 1.2 and more.

According to the invention the ratio q is selected in a range of $1.2 \leq q \leq 3.0$, in particular of $1.2 < q \leq 2.8$, preferably of $1.5 \leq q \leq 2.5$ and particularly preferably $1.8 \leq q \leq 2.2$.

In contrast to this, for coronary stents the value q is typically in a range of less than 1.2.

It has been shown, however, that with the smaller wall thicknesses of the coronary stent in comparison to the stent according to the invention for the paranasal sinus, the controlled release of active substance as desired according to the invention cannot be achieved.

The quotient q can thus serve as the calculation basis here. For example, for a hollow cylinder the volume V can be calculated from the height h, the internal diameter $r_i$ and q:

$$V = \pi \cdot h \cdot r_i^2 (q^2 - 1) \quad [1]$$

Formula 1 makes it clear that the volume of a coronary stent (with q=1.2), with the same internal diameter $r_i$ and the same height h is a maximum of about 15% of the volume of a paranasal sinus spacing device according to the invention (with q=2). It follows from this that stents with q=1.2 or less can receive a maximum of ⅐ of the active substance dose of a paranasal sinus spacing device according to the invention.

The quotient q has serious consequences for the release periods over which active substances can be released. To estimate the release duration t as a function of the thickness of a material l and the diffusion coefficients D, in the literature the dimensionless expression:

$$t = \frac{l^2}{D} \quad [2]$$

is used (Cussler, E. L.; Diffusion: Mass Transfer in Fluid Systems, Cambridge Univ. Press, 1996). The diffusion section in a hollow cylinder can be estimated as half the difference between external diameter $r_a$ and external diameter $r_i$. In a stent with a constant internal diameter $r_i$ the release duration is reduced to 4% when q is reduced from 2 to 1.2. For the above-mentioned reasons, for the described paranasal sinus spacing device the value q is preferably above 1.2 and in particular in a range $1.2 < q \leq 2.8$, particularly preferably $1.5 \leq q \leq 2.5$ and particularly preferably the range is $1.8 \leq q \leq 2.2$.

According to a further aspect, the invention relates to a spacing device for the paranasal sinus in which the layer or layers loaded with active substance are separated towards the inner cavity by a layer consisting of a material which is impermeable or at least virtually impermeable for the active substance. Active substance losses are thus avoided and the duration over which the active substance is released is simultaneously increased.

Serious differences also exist with respect to the mechanical properties. Coronary stents which are introduced via a catheter into the blood vessels have to be plastically, i.e. irreversibly deformable. Owing to an irreversible widening of the stent, they have to be fixed to the vessel wall.

The spacing device developed in the course of this invention for use in the paranasal sinus, in contrast thereto, is distinguished by elastic properties and therefore reversible deformability; the paranasal sinus spacing device can be fixed simply in the apertures to the paranasal sinus, inter alia owing to this elasticity.

It is possible with the spacing device (stent) loaded with active substance according to the invention to keep the frontal sinus accesses open not only by a physical/mechanical mechanism, but also by a pharmacological mechanism. These spacing devices are adapted to the surgically created accesses to the paranasal sinus and fulfil two functions:

1. They keep physically open the newly created "fenestration" of the front sinus in the course of the minimally invasive clearing. On the one hand, this is achieved by the application of the spacing device to the surgically changed tissue and assisted by the encouragement of the secretion drainage from the sinus.
2. The developed spacing devices may release active substances such as medicinal substances such as, for example corticosteroids which suppress tissue formation or overshooting wound healing and therefore keep open the surgically newly created fenestration.

In order to be able to fulfil both functions in an optimal manner, the "stent" has some design features which will be described in more detail hereinafter with the aid of the figures.

The spacing device according to the invention is a hollow body which is composed of a sheath surrounding an inner cavity and having a respective aperture at two opposing ends.

The hollow body is preferably based on a cylindrical shape wherein it can deviate from the ideal cylindrical form with an in particular uniform diameter along the shaft.

The external diameter along the cylinder shaft may thus vary, for example the external diameter in the end regions close to the apertures may be selected to be larger than in the central shaft region.

Starting from the end regions, the external diameter may continuously reduce in the direction of the central shaft region, may be reduced in the manner of an hourglass in the central region, wherein the specific shape of the cylindrical basic body can be adapted in any way as necessary.

The wall thickness of the cylinder may also be selected to be variable.

DESCRIPTION OF THE PREFERRED EMBODIMENTS

Figure 1:
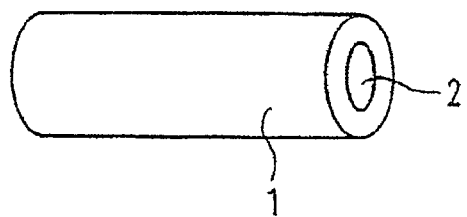
FIG. 1 shows a preferred configuration according to the invention of the spacing device in cylindrical form.

The geometry of the spacing device is preferably that of a hollow cylinder as can be seen in FIG. 1, wherein a sheath 1 surrounds an inner cavity having apertures 2 at the two opposing ends of the cylinder shaft. This cylinder form encourages the secretion drainage from the sinuses owing to its tubular design.

The length of the cylinder is preferably selected here in a range of 5 to 30 mm and its external diameter in a range of 1 to 30 mm. The wall thickness is to be selected according to need as a function of the physical properties of the polymer materials used and the active substances used and the desired release profile within the above-mentioned ranges for the ratio q of external diameter to internal diameter.

The at least two inner apertures 2 typically have a diameter in a range of 0.5 to 25 mm.

Figure 2:
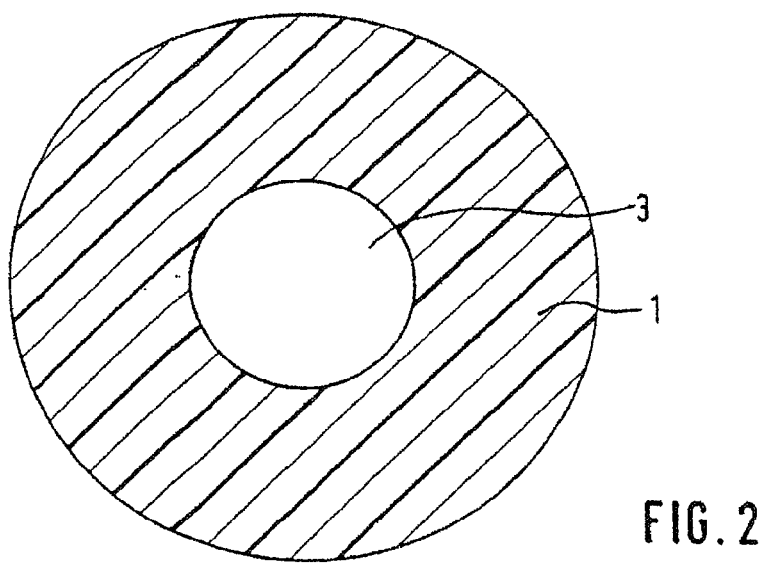
FIG. 2 shows a cross section through a spacing device loaded with active substance according to the invention.

FIG. 2 shows an example of a spacing device with a monolithic construction, wherein the sheath 1 is composed of a single layer and the layer material forms the matrix for the active substance.

Figure 3:
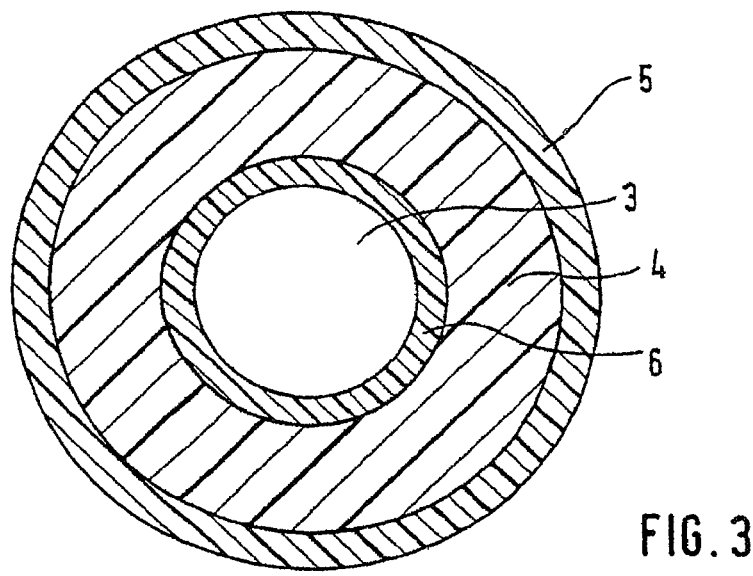
FIG. 3. shows a cross-section of another preferred configuration of the spacing device according to the invention as a reservoir system with a plurality of layers.

FIG. 3 shows an example of a configuration of the spacing device according to the invention as a reservoir system, wherein the active substance is contained in a reservoir 4. In this case the active substance is not contained in a matrix material, unlike in the matrix system. The active substance may here directly form the layer forming the reservoir or the active substance may be provided in a corresponding cavity. The latter case is suitable in particular for liquid or semi-solid active substances or for liquid or semi-solid carriers containing the active substance. The active substance to be released may also be dissolved or suspended in the reservoir system.

The release-controlling material forming the cavity, for example a reservoir 4 is surrounded by an outer membrane 5 which preferably consists of a polymer material through which the active substance can diffuse.

The cavity forming the reservoir 4 is preferably separated on the inside to the inner cavity 3 by an inner wall 6 preferably consisting of a material which is impermeable or virtually impermeable to the active substance.

An inner layer (inner wall 6) which is as impermeable as possible to the active substance is suitable in principle for any active substance-carrying systems for avoiding active substance losses in the direction of the inner cavity 3.

The inner wall 6 may consist of a corresponding polymer material, but also of an inorganic material, such as a metal, etc.

Figure 4:
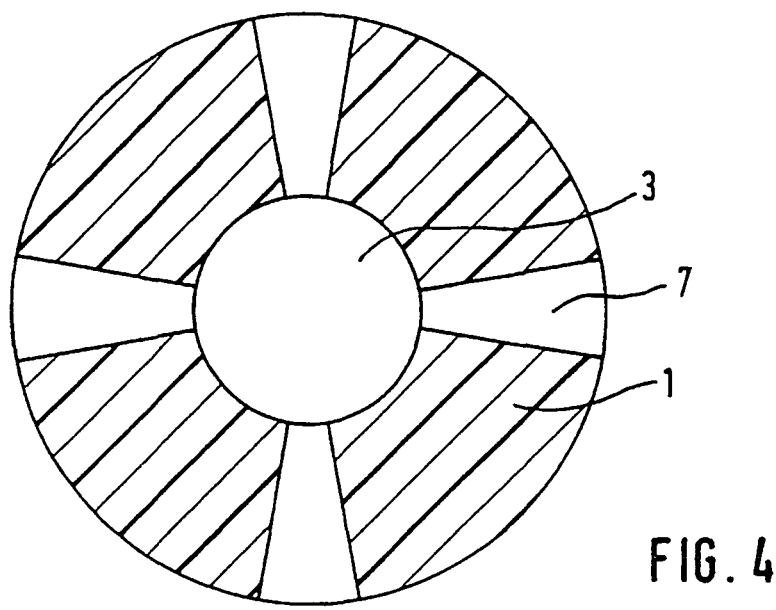
FIG. 4 shows a further configuration of the spacing device according to the invention with perforations in the sheath.

The sheath 1 may have perforations 7, as shown in FIG. 4, which connect the inner cavity 3 to the outer surface of the stent. The secretion drainage can also be assisted by this measure.

The form and number of perforations 7 can be freely selected here as required.

Figure 5:
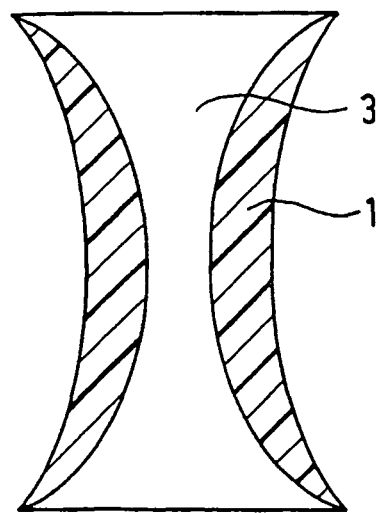
FIG. 5 shows a configuration of the spacing device according to the invention, wherein the external diameter of the cylindrical shaft in the end regions is greater than towards the centre and furthermore the wall thickness increases towards the centre of the cylinder shaft.

A configuration according to the invention with a varying external diameter is shown in FIG. 5. In the embodiment shown in FIG. 5, the external diameter of the stent is selected to be greater at the end regions with the apertures 2 than in the central region and decreases continuously towards the centre.

As shown here, the wall thickness may also vary, wherein it decreases in this case towards the end regions.

The wall thickness, in other words the ratio q of external diameter to internal diameter may, as required, in particular in the end regions or else in short central sections be outside the value to be adjusted according to the invention for q, if the usability of the stent is not impaired. Thus, at least in the wound regions q should be within the above-mentioned value range according to the invention of $1.2 \leq q \leq 3.0$. In the event that in individual regions of the hollow body the wall thickness has a value q outside the value range according to the invention, these regions or this range should not be more than 30% of the hollow body.

The stent according to the invention may be formed from one or more layers, wherein the layers may consist of the identical and/or different polymers. Individual regions of a layer, for example the end regions close to the apertures 2 may be manufactured from a material which is different from the material for the remaining layer regions. In other words one layer may contain at least one region which is formed from a different material than the remaining layer.

In addition, the stent according to the invention may have layers which are free of active substance in addition to layers which are loaded with active substance.

If necessary, the stent according to the invention may be surrounded by a suitable outer coating.

In contrast to coronary stents, the spacing device according to the invention does not necessarily lie homogenously and in a planar manner on the tissue. This circumstance requires a particular construction so that, for example, secretion cannot build up in the long term between the spacing device and the sinus wall. Secretion drainage can be facilitated by perforations 7 in the wall of the spacing device (see cross-section shown in FIG. 4). With respect to its form the spacing device may show an "hourglass-shaped" transition zone from the front sinus to the nasal interior (FIG. 5) and permits endoscopy of the sinus through a central aperture.

According to a further configuration, the space holder may have irregularities such as humps etc. on its outer surface. In this case, contact with the nasal wall is via these irregularities, wherein, on the one hand, the contact face can be reduced and an adequately firm hold is nevertheless ensured. The developing cavities between the outer surface of the stent and nasal wall simultaneously encourage secretion drainage.

The spacing device is moreover advantageously provided such that suction of the paranasal sinus remains possible owing to the spacing device. This is made possible owing to a relatively small length. The spacing device is therefore preferably constructed such that it can be cut to the desired length directly prior to application.

The spacing device must be "anchored" counter to gravity in the frontal sinus entry. This anchoring can be achieved by a "ballooning" of the implant, i.e. a widening of the spacing device end in the frontal sinus or fixing by means of a seam on the nasal septum. Moreover, the stent may consist of materials which favour anchoring and shape adaptation. In this context "shape memory polymers" (for example U.S. Pat. No. 5,139,832, U.S. Pat. No. 5,189,110) or swelling polymers can be used (for example DE 4 032 096).

While the former change their shape at body temperature, with swelling substances there is a volume increase of the material owing to water absorption and therefore an increase in the stent diameter after its application. The materials adapt optimally here to the defect and thus prevent slipping of the stent. Owing to their good permeability to water, swelling polymers prevent a build up of secretion at the contact face to the tissue.

Figure 6:
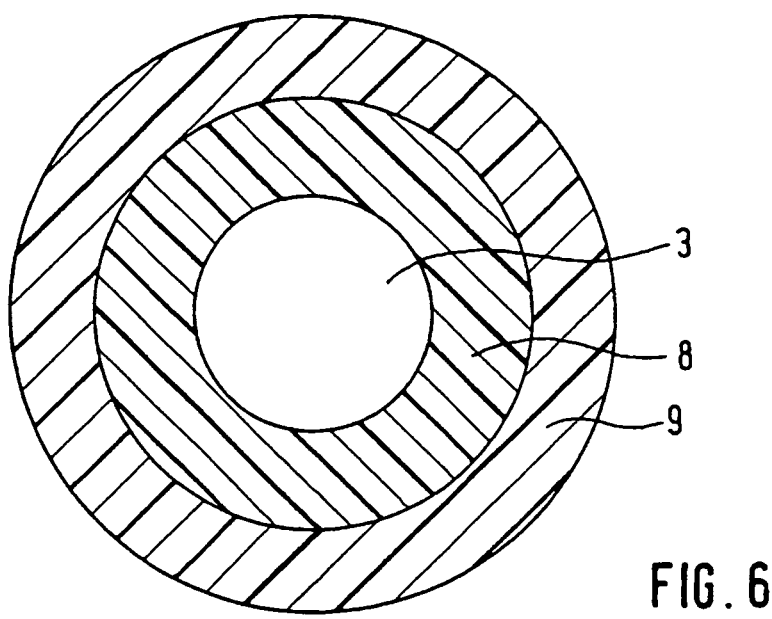
FIG. 6 shows a further configuration of the spacing device according to the invention as a matrix system with a plurality of layers.

An example of this is shown in FIG. 6, wherein the outer layer 9 consists of a deformable polymer and surrounds a polymer layer 8 loaded with active substance.

The spacing device in the nose, in contrast to spacing devices in vessels, is exposed to a bacteria-loaded environment (mucous membrane wounds with free contact to the outside air). Owing to corresponding shaping, scab formation and bacterial contamination is delayed. This may, for example, be achieved by an adequately large internal diameter of the spacing device encouraging secretion drainage. The materials used may moreover be modified at the surface in such a way that secretion drainage is encouraged and bacterial contamination is avoided. An example is the hydrophilising of the surface. For this purpose the interior of the hollow body can be lined with a polymer layer which is highly wettable and preferably has water contact angles <45°.

As an alternative thereto, polymers can be used, the surfaces of which have been chemically modified, such as, for example, by the chemical bonding of hydrophilic substances or by treatment with gas plasma.

To avoid any bacterial contamination the spacing device may also be loaded with bactericidally or bacteriostatically active substances.

In order to ensure the diverse functions of the stent, the design of the matrix system may above all consist of a plurality of polymer layers, as the cross-section in FIG. 6 shows by way of example. The number of layers is not limited to two as shown in the figure. Thus, a plurality of layers which fulfill different functions can be combined with one another. Individual layers may be fee of medicinal substance or be loaded with one or more medicinal substances. In loading different layers with various medicinal substances, the latter may be released from the spacing device with different kinetics. The thickness of individual polymer layers may be thin, as desired, for example in the range of a few micrometers.

The spacing device may also be already preformed prior to application or else be shaped to its final geometry by processing a precursor. Methods, such as, for example, extrusion or injection moulding are excellently suited to producing preformed spacing devices. For production from precursors polymer films may for example be rolled to form hollow bodies and fixed by a seam.

The materials from which the spacing device can be produced may be biodegradable or else non-biodegradable materials or a combination thereof.

Examples of possible biodegradable materials are polymers of lactic acid or glycolic acid and their copolymers. Further suitable examples are to be found in the literature (K. Park, W. S. W. Shalaby, H. Park, Biodegradable Hydrogels for Medicinal substance Delivery, Technomic Publishing Inc. Lancaster 1993; A. Domb, J. Kost, D. M. Wiseman, Handbook of Biodegradable Polymers, Harwood Academic Publishers, 1997).

While biodegradable materials have the advantage of not having to be removed after application, non-biodegradable materials can be better fixed in the region of use of the spacing device. Examples of such materials are silicones, polyacrylates and polymethacrylates and the copolymers thereof (Eudragit®)), poly(ethylene vinyl acetate) copolymer and other compositions as described in the polymer literature and known for medical applications.

The polymers should preferably be flexible so that they adapt to the wound area. Moreover, they should be elastic enough to remain in the fenestration and should be biocompatible, in other words have good tolerability with respect to cells and tissues. To ensure the mechanical adherence of the spacing device to the fenestration, the polymers mentioned can be combined with other materials, such as for example metals to ensure a reliable seat of the "stent" with smaller wall thicknesses. These metals can be incorporated into the wall of the cylinder.

The polymers can be processed by various industrial methods to form the spacing devices shown in FIGS. 1 and 2, thus, for example by extrusion or injection moulding or by polymerisation in suitable moulds.

The casting of polymer solutions is a simple production method (solvent casting). For this purpose the polymers are dissolved in organic solvents and the solution is poured or sprayed onto an inert surface. After evaporation of the solvent dry polymer films loaded with active substance are obtained which can be cut into any, for example rectangular forms.

While tubes are directly obtained by extrusion or injection moulding, small individually adapted tubes can be formed from rectangular polymer films directly before insertion into the patient. This may take place by repeated rolling of the polymer film or by mechanical adhesion or sticking of opposing film edges.

Owing to the type of production, the polymer properties can be controlled such that either smooth or porous surfaces are produced. This influences the rate of active substance administration and optionally the interaction between the spacing device and wound edges.

The surfaces of the spacing device towards the tissue and the secretion side may also be changed such that they optimally do justice to the requirements of their functions. The inside of the cylinder to the cavity of the spacing device may, for example be physico-chemically changed on its surface such that there can be improved wetting with secretion and therefore improved secretion drainage. Examples are the above-mentioned hydrophilising of surfaces or the covalent bonding of hydrophilic substances to the polymer surfaces.

The surface to the tissue side may be chemically changed such that the tissue compatibility is improved. This can be achieved by a coating with materials in the form of thin films or connection or application of functional groups or whole molecules which interact with the biological system. Thus the anchoring of polyethylene glycol chains to the surface leads to a reduced cell attachment and this facilitates the removal of the spacing device and increases it compatibility with the wound tissue.

The active substances can be selected according to need, application, desired property etc. They can also be used in combination. In particular, the stents according to the invention are loaded with medicinal substances.

Substances are generally used as medicinal substances which may influence the behaviour of cells and tissues, in particular they should prevent uncontrolled tissue growth. For this purpose, representatives of the group of glycocorticosteroids are suitable, such as for example cortisol, corisone, prednisone, prednisolone, 6-methylprednisolone, dexamethasone, fludrocortisone, desoxycorticoacetate. Further examples are proteins from the area of cytokines and growth factors which are also said to have some cell growth-inhibiting properties. Moreover, tyrosine kinase inhibitors, antisense-oligonucleotides and mitosis inhibitors such as mitomycin are suitable for eliminating the proliferative influence of growth factors during wound healing.

The active substances can be released from the spacing device over a long time period. Depending on the design and the material used, releases can be carried out for up to several years. Release preferably extends over a time period of 2 to 12 weeks. Principles controlling the release include, apart from the wall thickness expressed as the ratio q, primarily diffusion and polymer swelling for non-biodegradable polymers. When using biodegradable materials, i.e. those which dissolve during use, polymer erosion also plays an important part (Göpferich, Polymer Degradation and Erosion: Mechanismus and Applications, Eur. J. Pharm. Biopharm., 42 (1996) 1-11).

If the spacing device is produced from the preferred non-degradable materials, the active substance is preferably released from the reservoir or a matrix system. In both cases, the active substance is released in the process by diffusion. The release of active substance can be influence by a plurality of factors. By changing the geometry the active substance can be released over different lengths of time. Furthermore, it is possible to control the kinetics of the active substance release by the degree of loading.

The loading, in particular in the embodiment as a matrix system, is preferably in a range up to 30% by weight based on the total system. The minimum loading depends inter alia on the potency of the active substance and on the desired duration of release.

To further influence diffusion additives can be added to the polymer matrix or the polymers. Inert inorganic materials such as, for example silicone dioxide thus lead to a reduction in the rate of release. Depending on the type of polymer the rate of release can be increased by plasticiser additives. During polymer swelling, swelling can be increased by osmotic additives into the polymer and the rate of release can therefore be increased depending on the active substance properties.

To control the active substance release by erosion, the type of biodegradable polymer can be geared to the application. Thus, for example, it is known with poly(D,L-lactide-co-glycolide) that the rate of release and the rate of erosion can be controlled by the increase in the glycolide content.

The subject of the invention is a spacing device (stent) which after surgical opening of the paranasal sinus (mainly the frontal sinus) is inserted into the created fenestration to the nose. The newly developed spacing device prevents a postoperative scarred narrowing in that it combines two conventional treatment attempts for the surgically newly created frontal sinus access:
1. The spacing device acts as a physical barrier which mechanically keeps the access to the frontal sinus open.
2. The spacing device releases medicinal substances which control the growth of the tissue around the newly created access to the front sinus.

The material of the spacing device preferably has the mechanical properties of an elastomer such as, for example silicone, a proven material in ENT surgery for spacing devices. Owing to the preferred geometry which corresponds substantially to that of a hollow cylinder, secretion can drain from the sinuses. Moreover, the material acts as a local release system for medicinal substances such as for example corticosteroids. Owing to the shape and function the stent ensures a firm seat and simultaneously allows optimum secretion drainage. The continuous release of a defined quantity of medicinal substance is preferably ensured over a period of 8 weeks. The anticipated duration in position of the implant is preferably also 8 weeks. For production, films loaded with medicinal material, for example, can be rolled to form a cylinder and stabilised with a surgical seam. The spacing device is inserted intra operationem into the newly created frontal sinus access. If necessary, it is fixed in the operation area by its particular form, the materials used, its construction and/or by a surgical seam to prevent displacement. Apart from the use in fenestrations to the paranasal sinus, use is possible in the middle ear and the trachea.

1$^{st}$ Example

Production of a Dexamethasone-Loaded Polymer Film

The film has the following composition:

| | |
|---|---|
| Evatane 40-55 (purified with acetone) | 17.955 g |
| Dexamethasone DAB 10/Ph. Eur. | 0.045 g |
| Dichloromethane p.A. | 98 ml |
| Acetone p.A. | 4.5 ml |

The polymer used, a poly(ethylene-vinyl acetate) copolymer, is initially freed of additives which were added during the production of Evatane 40-55. Fifty g of Evatane 400-55 are also weighted out into a 500 ml iodine measuring cylinder with a magnetic stirring rod. Two hundred fifty ml acetone p.a. are measured with a measuring cylinder and added to the polymer. The batch is stirred on the magnetic stirrer for about a week and the acetone is then decanted. The polymer is washed three times with 80 ml acetone p.a. and the washing liquid discarded. The extraction and washing procedure is repeated once with acetone and twice with ethanol using the same volumes. The polymer is then dried in a crystallising dish in a laminar airflow box for 48 h and then in a desiccator under vacuum.

17.955 g Evatane 40-55 are then weighed out into a 250 ml iodine value vessel. The dichloromethane is added thereto and stirred on the magnetic stirrer over 12 h. The dexamethasone is dissolved in acetone and added to the polymer solution. The batch is then left to stand for 10 min without stirring to remove air bubbles. The solution is poured into a planar Teflon mould with an area of 15 cm² and dried in a laminar airflow box over 4 days.

The dried film is drawn from the Teflon mould and cut into pieces of any size. The film thickness is about 0.8 to 1 mm. The polymer films are rolled to form a hollow cylinder and preferably fixed by a seam with a biocompatible seam material at the contact points in such a way that the cylinder does not unwind owing to the elasticity of the material. The small tube formed in this way is then inserted into the fenestration to the paranasal sinus.

2$^{nd}$ Example

Release of Dexamethasone from the Polymer Film in Example 1

Figure 7:
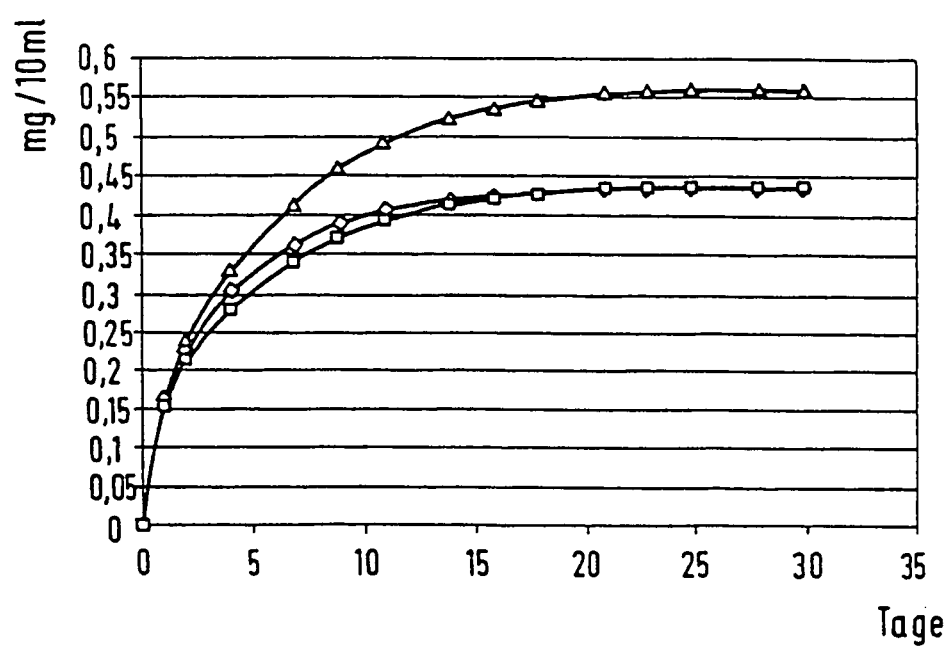
FIG. 7 is a graph with the release curve of an active substance from a preferred layer material according to the invention.

Round pieces with a diameter of 1.2 cm in diameter were cut from the film described in Example 1 and the release determined in vitro. The polymer platelets loaded with 0.25% dexamethasone were also stored in closable glass vessels in 10 ml phosphate buffer at 37° C. Samples were removed from the batch at regular intervals and replaced by fresh buffer. The dexamethasone content was determined per HPLC. FIG. 7 shows the release of dexamethasone over the time.

LIST OF REFERENCE NUMERALS 1 sheath
2 aperture
3 inner cavity
4 reservoir area
5 membrane
6 layer impermeable to active substance
7 perforation
8 polymer layer loaded with active substance
9 deformable polymer layer

The invention claimed is:

1. A substance delivering spacer device for implantation in an opening of a paranasal sinus, said device comprising:
   a tubular body having a wall, a hollow passage extending therethrough and being open at either end and perforations formed in the wall through which bodily secretions may flow into the hollow passage, the wall of said tubular body comprising:
   an inner layer comprising a polymer that is devoid of therapeutic substance;
   an outer layer comprising a polymer that is devoid of therapeutic substance; and
   a therapeutic substance containing layer located between the inner and outer layers, said therapeutic substance containing layer being substantially solid and comprising a polymer combined with a therapeutic substance such that the therapeutic substance will elute therefrom when the device is implanted;
   wherein said outer layer is constructed to allow a therapeutically effective amount of the therapeutic substance to elute through the outer layer and from the device while implanted,
   wherein said inner layer is substantially impervious to the therapeutic substance,
   wherein said therapeutic substance comprises at least one steroid;
   said tubular body being flexible and sufficiently elastic to frictionally engage and remain in the opening following its insertion into the opening; and the device having an outer diameter $r_a$ and an inner diameter $r_i$, wherein the ratio Q of the outer diameter $r_a$ to the inner diameter $r_i$ is greater than or equal to 1.2 but less than or equal to 3.0.

2. A device according to claim 1 wherein the substance elutes from the device over a period of from 2-12 weeks following implantation of the device.

3. A device according to claim 1 wherein at least a portion of the device is biodegradable.

4. A device according to claim 3 wherein erosion of a biodegradable portion of the device results in release of the substance from the device.

5. A device according to claim 1 wherein the device has a substantially constant outer diameter over its entire length.

6. A device according to claim 1 wherein the device has regions of differing outer diameter.

7. A device according to claim 6 wherein the ends of the device are larger in outer diameter than the remainder of the device.

8. A device according to claim 1 wherein the polymeric material comprises poly(ethylene-vinyl acetate) copolymer.

9. A device according to claim 8 wherein the polymeric material also contains one or more additives to affect the rate at which the substance is released from the substance containing layer.

10. A device according to claim 8 wherein the therapeutic substance accounts for up to 30% of the total weight of the substance containing layer.

11. A device according to claim 1 wherein at least the outer surface of the device is formed from a material selected from biodegradable polymers, non-biodegradable polymers, shape memory materials and formable materials.

12. A device according to claim 1 wherein the inner layer, the substance containing layer and the outer layer each comprises a substantially solid polymer.

13. A device according to claim 12 wherein the substance containing layer and the outer layer are formed substantially of the same polymer.

14. A device according to claim 12 wherein the substance containing layer and the outer layer are formed of different polymers.

15. A device according to either of claim 13 or 14 wherein the polymer or polymers is/are selected from the group consisting of: poly(alpha-hydroxy esters), polyacrylates, ethylene vinyl acetate copolymer and silicone.

16. A device according to claim 1 wherein the therapeutic substance further comprises at least one additional agent selected from the group consisting of: bacteriocides, bacteriostats and mixtures thereof.

17. A device according to claim 1 further comprising a coating disposed on the device to improve biocompatibility.

18. A device according to claim 1 wherein said at least one steroid comprises a glucocorticoid.

19. A device according to claim 1 wherein said at least one steroid comprises a steroid selected from the group consisting of: cortisol, corisone, prednisone, prednisolone, 6-methylprednisolone, dexamethasone, fludrocortisone, desoxycorticoacetate.

20. A method for treating a disorder that affects a paranasal sinus, middle ear or trachea, said method comprising the steps of
   A) providing a substance delivering spacer device for implantation in an opening of a paranasal sinus, said device comprising:
      a tubular body having a side wall, a hollow passage extending therethrough and being open at either end and perforations formed in the wall through which bodily secretions may flow into the hollow passage, the wall of said tubular body comprising:
      an inner layer comprising a polymer that is devoid of therapeutic substance;
      an outer layer comprising a polymer that is devoid of therapeutic substance; and
      a therapeutic substance containing layer located between the inner and outer layers, said therapeutic substance containing layer being solid and comprising a polymer combined with a therapeutic substance such that the therapeutic substance will elute therefrom when the device is implanted;
      wherein said outer layer is constructed to allow a therapeutically effective amount of the therapeutic substance to elute through the outer layer and from the device while implanted,
      wherein said inner layer is substantially impervious to the therapeutic substance,
      wherein said therapeutic substance comprises at least one steroid;
      said tubular body being flexible and sufficiently elastic to frictionally engage and remain in the opening following its insertion into the opening; and
      the device having an outer diameter $r_a$ and an inner diameter $r_i$, wherein the ratio Q of the outer diameter $r_a$ to the inner diameter $r_i$ is greater than or equal to 1.2 but less than or equal to 3.0; and B) implanting the device in an opening of a paranasal sinus such that a therapeutic amount of the therapeutic substance is delivered to the opening of a paranasal sinus in which the device is implanted.

21. A method according to claim 20 wherein Step B comprises implanting the device in an opening of a frontal sinus.

22. A method according to claim 20 wherein Step B comprises implanting the device in an opening of a paranasal sinus that has been dilated.

23. A method according to claim 20 wherein Step B comprises implanting the device in an opening of a paranasal sinus that has been surgically altered.

24. A method according to claim 20 wherein the device is implanted in a surgically created fenestration.

25. A method according to claim 20 wherein the device is capable of being radially expanded and wherein Step B comprises radially expanding the device at an intended site of implantation.

26. A method according to claim 25 wherein the device is radially expanded by inflating a balloon positioned within the device.

27. A method according to claim 20 further comprising the step of:

C) removing the device.

28. A method according to claim 27 wherein the device is removed approximately 2 to 12 weeks after implantation.

29. A system comprising a substance delivering spacer device according to claim 1 in combination with a balloon that is positionable and inflatable within the hollow passage of the substance delivering spacer device to widen at least a portion of the substance delivering spacer device.

* * * * *